United States Patent
Jain et al.

(10) Patent No.: US 10,760,117 B2
(45) Date of Patent: Sep. 1, 2020

(54) METHODS FOR DETERMINING BASE LOCATIONS IN A POLYNUCLEOTIDE

(71) Applicant: THE REGENTS OF THE UNIVERSITY OF CALIFORNIA, Oakland, CA (US)

(72) Inventors: Miten Jain, Santa Cruz, CA (US); Hugh Edward Olsen, Santa Cruz, CA (US); Mark A. Akeson, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 20 days.

(21) Appl. No.: 15/564,386

(22) PCT Filed: Apr. 5, 2016

(86) PCT No.: PCT/US2016/026047
§ 371 (c)(1),
(2) Date: Oct. 4, 2017

(87) PCT Pub. No.: WO2016/164363
PCT Pub. Date: Oct. 13, 2016

(65) Prior Publication Data
US 2018/0258474 A1  Sep. 13, 2018

Related U.S. Application Data

(60) Provisional application No. 62/143,585, filed on Apr. 6, 2015.

(51) Int. Cl.
*C12Q 1/6827*  (2018.01)
*C12Q 1/6869*  (2018.01)

(52) U.S. Cl.
CPC ......... *C12Q 1/6827* (2013.01); *C12Q 1/6869* (2013.01); *C12Q 2521/531* (2013.01);
(Continued)

(58) Field of Classification Search
CPC ............... C12Q 1/6827; C12Q 1/6869; C12Q 2521/531; C12Q 2525/119;
(Continued)

(56) References Cited

U.S. PATENT DOCUMENTS 8,822,146 B2 *  9/2014  Klimasauskas .......... C12Q 1/48
                                                          435/193
9,121,061 B2 *  9/2015  Vaisvila ............... C12Q 1/6869
(Continued)

FOREIGN PATENT DOCUMENTS

WO     2013185137      12/2013
WO     2013191793      12/2013
(Continued)

OTHER PUBLICATIONS

Do et al. Oncotarget. 2012. 3:546-558. (Year: 2012).*
(Continued)

*Primary Examiner* — Joseph G. Dauner
(74) *Attorney, Agent, or Firm* — Shweta Chandra; Bozicevic, Field & Francis LLP

(57) ABSTRACT

Disclosed are methods for polynucleotide sequencing that detect the location of selected nucleobases with greater precision. The methods can be used to determine the location and nature of modified bases in a polynucleotide, that is, non-canonical bases, or to improve accuracy of sequencing of "problem" regions of DNA sequencing such as homopolymers, GC rich areas, etc. The sequencing method exemplified is nanopore sequencing. Nanopore sequencing is used to generate a unique signal at a point in a polynucleotide sequence where an abasic site (AP site, or apurinic or apyrimidinic site) exists. As part of the method, an abasic site is specifically created enzymatically using a DNA glycosylase that recognizes a pre-determined nucleobase
(Continued)

species and cleaves the N-glycosidic bond to release only that base, leaving an AP site in its place.

12 Claims, 13 Drawing Sheets

Specification includes a Sequence Listing.

(52) U.S. Cl.
CPC .. *C12Q 2525/119* (2013.01); *C12Q 2537/164* (2013.01); *C12Q 2563/116* (2013.01); *C12Q 2565/631* (2013.01)

(58) Field of Classification Search
CPC ........ C12Q 2537/164; C12Q 2563/116; C12Q 2565/631
See application file for complete search history.

(56) References Cited

U.S. PATENT DOCUMENTS

| | | | | |
|---|---|---|---|---|
| 10,155,939 | B1* | 12/2018 | Vaisvila | C12N 9/88 |
| 2006/0134631 | A1 | 6/2006 | Krokan et al. | |
| 2006/0177867 | A1* | 8/2006 | Evans | C12Q 1/6844 |
| | | | | 435/6.18 |
| 2011/0224105 | A1* | 9/2011 | Kurn | C12P 19/34 |
| | | | | 506/26 |
| 2011/0245309 | A1 | 10/2011 | Sobol et al. | |
| 2012/0091005 | A1* | 4/2012 | Burrows | B82Y 15/00 |
| | | | | 204/605 |
| 2012/0237943 | A1 | 9/2012 | Aleksey et al. | |
| 2013/0177921 | A1* | 7/2013 | Chastain | C12Q 1/68 |
| | | | | 435/6.19 |
| 2013/0303385 | A1 | 11/2013 | Aleksey et al. | |
| 2014/0178881 | A1 | 6/2014 | Booth et al. | |
| 2016/0222444 | A1* | 8/2016 | Gundlach | B01D 57/02 |
| 2018/0164280 | A1* | 6/2018 | Ecker | G01N 33/48721 |

FOREIGN PATENT DOCUMENTS

| | | |
|---|---|---|
| WO | 2014071250 | 8/2014 |
| WO | 2015031909 | 3/2015 |

OTHER PUBLICATIONS

Yokota et al. RSC Adv. 2014. 4:15886-15899 (first published Mar. 13, 2014) (Year: 2014).*
Caulfied et al. Journal of Biological Chemistry. 1998. 275:12689-12695. (Year: 1998).*
Moyer et al. Mutation Research/Fundamental and Molecular Mechanisms of Mutagenesis. 1993. 225:291-300. (Year: 1993).*
An et al. PNAS. 2012. 109(29):11504-11509. (Year: 2012).*
Insert for EPIQUIK DNA Demethylase Activity/inhibition Assay Ultra Kit. Retrieved on Apr. 10, 2020 from the internet: https://www.epigentek.com/docs/P-3008.pdf) (Year: 2020).*
Schreiber et al. PNAS. 2013. 110(47):18910-18915. (Year: 2013).*
He et al. Science. 2011. 333(6047):1303-1307. (Year: 2011).*
Shen et al. Current Opinion in Cell Biology. 2013. 25:289-296. (Year: 2013).*
Gromenko et al. (2009) "Deamination of 5-Methylcytosine Residues in Mammalian Cells," Acta Naturae, vol. 1, No. 3, pp. 121-124.
Sagi et al. (2000) "Differential Destabilization of the DNA Oligonucleotide Double Helix by a T.G Mismatch, 3, N-Ethenocytosine, 3, N-Ethanocytosine, or an 8-(Hydroxymethyl)-3, Nethenocytosine Adduct Incorporated into the Same Sequence Contexts," Chem. Res. Toxical. vol. 13, No. 9, pp. 839-845.
An et al. (2012) "Modulation of the current signatures of DNA abasic site adducts in the α-hemolysin ion channel" Chem. Comm., 48(93):11410.
Clarke et al. (2009) "Continuous base identification for single-molecule nanopore DNA sequencing" Nature Nanotechnology, 4(4):265-270.
Wallace et al. (2010) "Identification of epigenetic DNA modifications with a protein nanopore" Chemical Comm., 46(43):8195-8197.
Wolna et al. (2013) "Electrical Current Signatures of DNA Base Modifications in Single Molecules Immobilized in the α-Hemolysin Ion Channel" Israel Journal of Chem., 53(6-7):417-430.

* cited by examiner

Structures of Cytosine and Modified Cytosines

```
                         SEQUENCE LISTING

<160> NUMBER OF SEQ ID NOS: 10

<210> SEQ ID NO 1
<211> LENGTH: 47
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (11)..(11)
<223> OTHER INFORMATION: 5-methyl-2'-deoxycytidine
<220> FEATURE:
<221> NAME/KEY: misc_feature
<222> LOCATION: (36)..(36)
<223> OTHER INFORMATION: n is abasic nucleotide

<400> SEQUENCE: 1 ttttttttc cggttttttt ttccggtttt ttttcnggtt ttttttt               47

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (14)..(14)
<223> OTHER INFORMATION: n is non-standard base

<400> SEQUENCE: 2
acccgtaacc gtantcgcgt aaa                                         23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
tttacgcgaa tacggttacg ggt                                         23

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (14)..(14)
<223> OTHER INFORMATION: n is abasic nucleotide

<400> SEQUENCE: 4
acccgtaacc gtantcgcgt aaa                                         23

<210> SEQ ID NO 5
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (10)..(10)
<223> OTHER INFORMATION: n is abasic nucleotide

<400> SEQUENCE: 5
acccgtaacn ggattcgcgt aaa                                              23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
acccgtaact ggattcgcgt aaa                                              23

<210> SEQ ID NO 7
<211> LENGTH: 23
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
tttacgcgaa tccggttacg ggt                                              23

<210> SEQ ID NO 8
<211> LENGTH: 23
<212> TYPE: RNA
<213> ORGANISM: Artificial Sequence
<220> FEATURE:
<223> OTHER INFORMATION: Description of Artificial Sequence: Synthetic
      polynucleotide

<400> SEQUENCE: 8
ucccguggcc guaggcgcgu cgg                                              23

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (11)..(11)
<223> OTHER INFORMATION: n is non-standard base

<400> SEQUENCE: 9
ccgacgcgcc nacggccacg gga                                              23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      polynucleotide
```

```
<220> FEATURE:
<221> NAME/KEY: misc_feature
<222> LOCATION: (11)..(11)
<223> OTHER INFORMATION: n is abasic nucleotide

<400> SEQUENCE: 10
ccgacgcgcc nacggccacg gga                                              23
```

METHODS FOR DETERMINING BASE LOCATIONS IN A POLYNUCLEOTIDE

CROSS-REFERENCE TO RELATED APPLICATIONS

This application claims priority from U.S. Provisional Patent Application No. 62/143,585 filed on Apr. 6, 2015, which is hereby incorporated by reference in its entirety.

STATEMENT OF GOVERNMENTAL SUPPORT

This invention was made with government support under contracts HG006321 and HG00782 awarded by the National Institutes of Health, National Genome Research Institute. The government has certain rights in the invention.

REFERENCE TO SEQUENCE LISTING, COMPUTER PROGRAM, OR COMPACT DISK

The instant application contains a Sequence Listing which has been submitted electronically in ASCII format and is hereby incorporated by reference in its entirety. Said ASCII copy, created on Mar. 28, 2016, is named 482_41_PCT_seq_list.txt and is 3,234 bytes in size.

BACKGROUND OF THE INVENTION

Field of the Invention

The present invention relates to the field of polynucleotides (e.g. DNA, RNA) and the field of polynucleotide sequencing (e.g. nanopore sequencing).

Related Art

Presented below is background information on certain aspects of the present invention as they may relate to technical features referred to in the detailed description, but not necessarily described in detail. That is, individual compositions or methods used in the present invention may be described in greater detail in the publications and patents discussed below, which may provide further guidance to those skilled in the art for making or using certain aspects of the present invention as claimed. The discussion below should not be construed as an admission as to the relevance or the prior art effect of the patents or publications described.

BRIEF SUMMARY OF THE INVENTION

The following brief summary is not intended to include all features and aspects of the present invention, nor does it imply that the invention must include all features and aspects discussed in this summary.

The present invention in general concerns polynucleotide sequencing, wherein said sequencing can detect the identity and location of non-canonical bases with high accuracy, using the distinct characteristic of an abasic site within a polynucleotide sequence.

The present invention comprises, in certain aspects, a method for detecting a sequence of a polynucleotide molecule, comprising: (a) preparing a polynucleotide molecule which contains an abasic site; and b) conducting single molecule sequencing on the polynucleotide molecule prepared in step (a), including determining a sequence that comprises the abasic site, whereby the abasic site is identified within the sequence, whereby the abasic site may be correlated with a nucleotide in a reference sequence.

The invention further comprises, with the foregoing, a method further comprising a step of treating the polynucleotide molecule with a reagent that specifically acts on a specific nucleobase species to create said abasic site. The nucleobase species may be one of A, T, G, C, 5-methylcytosine, U, or another nucleobase species as described below. The invention further comprises, with the foregoing, a method wherein the reagent is a glycosylase that removes the specific nucleobase species from a sugar in the polynucleotide backbone. The invention further comprises, with the foregoing, a method wherein said abasic site is correlated to one of (a) a non-canonical base; and (b) a location of an A, T, C, or G base in a sequence. The invention further comprises, with the foregoing, a method comprising a step of correlating an abasic site to a location within a homopolymeric stretch in said polynucleotide molecule. The invention further comprises, with the foregoing, a method comprising a step of correlating an abasic site to an epigenetic modification. The invention further comprises, with the foregoing, a method wherein said epigenetic modification is one of 5-methylcytosine (5mC), 5-hydroxymethylcytosine (5hmC), 5-formyl cytosine (5fC) and 5-carboxycytosine (5caC). The invention further comprises, with the foregoing, a method comprising the step of correlating an abasic site to DNA damage of DNA adducts, 8-oxo-guanine, alkylated bases, ethenoadducts, and thymine dimers.

The invention further comprises, with the foregoing methods, a method wherein the single molecule sequencing is nanopore-based sequencing comprises measuring an ionic current that identifies an abasic site. The invention further comprises, with the foregoing, a method wherein the nanopore-based sequencing includes detecting an ionic current through a nanopore through which the polynucleotide passes.

In certain aspects, the present invention comprises a method for detecting a sequence in a polynucleotide, comprising: (a) treating a polynucleotide molecule with a glycosylase that creates an abasic site corresponding to a predetermined nucleobase species in the polynucleotide; (b) conducting sequencing on the polynucleotide prepared in step (a), wherein the sequencing indicates an abasic site within the polynucleotide sequence; and (c) using the sequence from step (b) to identify the abasic site and correlating said abasic site to said predetermined nucleobase.

The invention further comprises, with the foregoing, a method wherein the predetermined nucleobase species is one of uracil, 5-methylcytosine (m5C), 5,6-Dihydrouracil, 5-Hydroxymethylcytosine, hypoxanthine and xanthine. The invention further comprises, with the foregoing, a method wherein the polynucleotide molecule is RNA and the predetermined nucleobase species is one or more of pseudouridine (Ψ), dihydrouridine (D), inosine (I), and 7-methylguanosine (m7G). The invention further comprises, with the foregoing, a method further comprising the step of treating the polynucleotide with a reagent that modifies a specific predetermined nucleobase species to a different species of nucleobase by acting on the nucleobase, and then treating the polynucleotide molecule with said glycosylase, wherein said glycosylase acts on the different species of nucleobase. The invention further comprises, with the foregoing, a method wherein the reagent is 5 methyl-cytosine deaminase and the glycosylase is G/T(U)-mismatch DNA glycosylase. The invention further comprises, with the foregoing, a method the reagent is $KRuO_4$ (potassium perruthenate) (to convert the 5-hydroxymethylcytosine bases to 5-formylcytosine). The invention further comprises, with the foregoing, a method wherein the glycosylase is one that lacks beta-lyase activity. The invention further comprises, with the foregoing, a method wherein the glycosylase is mutated to lack beta-lyase activity.

The invention further comprises, with the foregoing a method wherein the glycosylase and substrate converted to an abasic site is as follows: uracil-DNA glycosylase (substrate being uracil, 5-fluorouracil, isodiauric acid, 5-hydroxyuracil, alloxan), G/T(U)mismatch-DNA glycosylase (G/G, A/G, T/C, T/U and U/C mismatches, uracil mismatch) alkylbase-DNA glycosylases (3-methyl guanine, O2-Alkylcytosine, 5-formyluracil, 5-hydroxymethyluracil, hypoxanthine, N6-ethenoadeinine, N4-ethenocytosine, 7-chloroethyl-guanine, 3-Methyladenine, 7-chloroethyl-guanine, 8-oxoguanine); 5-methylcytosine-DNA glycosylase (T in G/T mismatch, and 5-methylcytosine thymine DNA glycosylase, 5-formylmethylcytosine (5fC), 5-carboxylcytosine (5caC)); adenine-specific mismatch DNA glycosylases (in G/A and C/A, and 8-oxoguanine); DNA Glycosylases removing oxidized pyrimidines (EndoIII-like) (5-hydroxycytosine, 5,6-Dihydrothymine, 5-Hydroxy-5,6-dihydrothymine, Thymine glycol, Uracil glycol, Alloxan, 5,6-Dihydroxyuracil, 5-Hydroxy-5,6-dihydroxyuracil, 5-Hydroxyuracil, 5-Hydroxyhydantoin, 2,5-Amino-5-formamidopyrimindine, 4,6-Diamino-5-formamidopyrimidine, 2,6-Diamino-4-hydroxy-5-foramimidopyrimidine; EndoVIII (5,6-dihydrothymine, thymine glycol); EndoIX (urea); hydroxymethyl-DNA glycosylase (uracil, 5-hydroxymethyluracil); hydroxymethyl-DNA glycosylase (uracil, 5-hydroxymethyluracil); formyluracil-DNA glycosylase (5-formyluracil); DNA glycosylases removing oxidized purines (8-oxoguanine, 2,5-Amino-5-formamidopyrimidine, 4,6-Diamino-5-formamidopyrimidine, 2,6-Diamino-4-hydroxy-5-foramimidopyrimidine 8-oxoguanine (opposite T), 8-oxoguanine (opposite A); and pyrimidine-dimer-DNA glycosylases (4,6-diamino-5-formamidopyrimidine, cyclobutane-pyrimidine dimer.

The present invention further comprises, in certain aspects, a method for preparing a naturally occurring polynucleotide for sequencing, said naturally occurring sequence comprising a non-canonical base in the polynucleotide, comprising the steps of treating the polynucleotide with a glycosylase enzyme to create an abasic site, and detecting the abasic site. The invention further comprises, with the foregoing, a method wherein the glycosylase is one of uracil-DNA glycosylase or 5-methylcytosine DNA glycosylase. The invention further comprises, with the foregoing a method further comprising the step of treating the polynucleotide with an enzyme to modify a specific base species and then removing bases modified by the enzyme with said glycosylase enzyme.

The present invention further comprises, in certain aspects, a method for preparing a polynucleotide for sequencing, said polynucleotide comprising a sequence of canonical bases, comprising the step of modifying selected canonical bases with a glycosylase enzyme that removes the selected bases from the polynucleotide to create abasic sites within the polynucleotide.

The present invention further comprises, in certain aspects, a method for improving sequence accuracy in a naturally occurring polynucleotide, comprising: (a) conducting a first sequencing of the polynucleotide; (b) treating a copy of the polynucleotide to remove a portion of bases having a predetermined structure of one of A, T, C, or G; (c) conducting a second sequencing of a polynucleotide treated in step (b) and identifying abasic sites corresponding to said predetermined structure; and (d) comparing results of the first sequencing and the second sequencing and correlating abasic sites found in the second sequencing with predetermined sites in the first sequencing, said comparison providing improved sequence accuracy. The invention further comprises, with the foregoing a method comprising converting a number of cytosine bases to 5-methylcytosine and removing the 5-methyl cytosine with 5-methyl cytosine glycosylase to create abasic sites at the locations of cytosines.

The present invention further comprises, in certain aspects, a kit for sequencing polynucleotides comprising a nanopore sequencing device, an enzyme selected from the group consisting of uracil-DNA glycosylase, G/T(U)mismatch-DNA glycosylase, alkylbase-DNA glycosylase, 5-methylcytosine-DNA glycosylase, thymine DNA glycosylase, adenine-specific mismatch DNA glycosylase, Fpg/Nei DNA glycosylase, Endonuclease III, Endonuclease VIII, Endonuclease IX, hydroxymethyl-DNA glycosylase, formyluracil-DNA glycosylase, formamidopyrimidine-DNA glycosylase, Fpg protein, Nei protein, and pyrimidine-dimer-DNA glycosylase; and instructions for detection of abasic sites by the nanopore sequencing device.

The present invention further comprises, in certain aspects, a computer program operative with a nanopore sequencing device for sequencing of polynucleotides containing abasic sites, comprising: (a) a look-up table with ionic current values for both (i) canonical base sequences and (ii) base sequences that include abasic sites at various positions in otherwise canonical base sequences; and (b) an algorithm applying the look-up table to translate ionic current values into a base sequence that includes the position of abasic sites in the sequenced DNA strand. The invention further comprises, with the foregoing computer program wherein the algorithm implements a hidden Markov model.

BRIEF DESCRIPTION OF THE DRAWINGS

FIG. 1A is a schematic diagram showing a polynucleotide having sites 1 and 3 occupied by specific nucleobases bases (e.g. A, T, G, C,), while site 2 in the polynucleotide contains an abasic site. A predetermined nucleobase species has been removed as shown at 102. In some cases, such as analyzing homopolymeric stretches (e.g. 5, 10, 20 etc. of the same repeating base species, such as poly T or poly C), some, but not necessarily all, of the predetermined polynucleobases will be removed. As shown at 104, FIG. 1A bottom panel, the polynucleotide is analyzed using a nanopore-based sequencing method. A nanopore-based sequencing procedure is used, where bases are sequentially interrogated, individually or in groups. A sequence signal, such as a difference in current though a pore, electrical property or the like, is generated based on the sequence. The sequence signal is analyzed by appropriate logic means (hardware or software processing signals from the detector) to produce a distinct signal for individual bases, wherein the location of the abasic site replacing the modified base is determined, along with canonical bases.

FIG. 1B illustrates a set of traces showing the ionic current difference between cytosine, 5-methylcytosine, and an abasic site in a nanopore based sequencer. Shown are ionic currents for 3 different DNA polynucleotides of the sequence- TTTTTTTTTC5mCGGTTTTTTTTTCCGGTTTTTTT TCabasicGGTTTTTTTTT (SEQ ID NO: 1). Of note is the consistent ~20 pA increase in ionic current when either a cytosine or a 5-methylcytosine is converted to an abasic position. Each of Events 1, 2 and 3 (top panel, middle panel and bottom panel of FIG. 1B) represents a single DNA strand analyzed in the nanopore device.

In FIG. 2 step 1, the non-standard base X is converted into an abasic site by the reaction of the polynucleotide with specific DNA glycosylase, such as listed here and further listed in Table 1. Specific DNA glycosylases include but are not limited to, 5-methylcytosine DNA glycosylase, uracil DNA glycosylase, G/T(U) mismatch DNA glycosylase, alkylbase DNA glycosylases, DNA glycosylases removing oxidized pyrimidines, DNA glycosylases removing oxidized purines (e.g. endonuclease III (Endo III) and Formamidopyrimidine-N-glycosylase [Fpg]), hydroxymethyl-DNA glycosylase, formyluracil-DNA glycosylase, and pyrimidine-dimer-DNA glycosylases. The example sequences shown have the sequences ACCCGTAACCGTAXTCGCGTAAA (strand to be sequenced; SEQ ID NO: 2), TTTACGCGAATACGGTTACGGGT (complementary strand; SEQ ID NO: 3), and ACCCGTAACCGTAabasicTCGCGTAAA (strand to be sequenced, with abasic site; SEQ ID NO: 4). In step 2, the sequence of the polynucleotide having the abasic sites is detected by a nanopore sequencing device, exemplified by a MINION™ sequencing device, made by Oxford Nanopore Technologies, Oxford, UK. Such a device and its use are described, e.g. in "Improved data analysis for the MINION™ nanopore sequence," Jain et al. Nature Methods 12:351-356 (2015) and in "Poretools: a toolkit for analyzing nanopore sequence data." Nicholas J. Loman & Aaron R. Quinlan. Bioinformatics, 30(23) 3399-3401 (2014). The bottom panel shows high current abasic sites.

| | |
|---|---|
| Step A | Beginning with native Lambda DNA, use PCR to copy Lambda DNA with 4 canonical dNTPs and dUTP. (top panel) |
| Step B | Take copied DNA with 4 canonical bases and replace U replacing T at randomly distributed portions. |
| Step C | Treat uracil containing DNA with uracil DNA glycosylase (UDG) |
| Step D | UDG creates abasic sites in copied DNA at positions previously containing uracil. |
| Step E | Obtain raw data from nanopore sequencing of DNA from steps A and D shows current spikes at abasic positions (bottom panel). |

Figure 3:
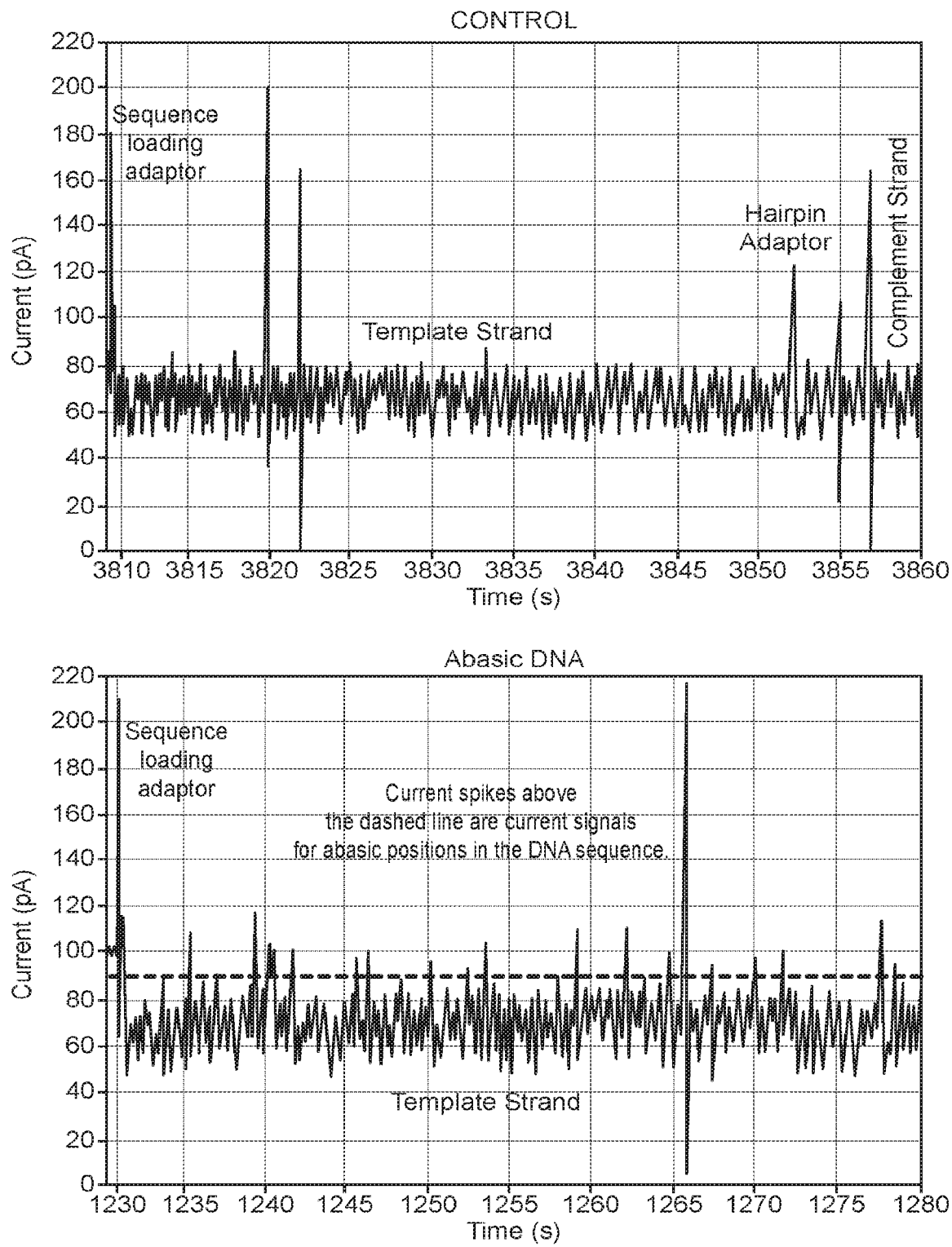
FIG. 3 is a pair of panels that show raw data from single control Lambda DNA molecules with no dUDP or glycosylase (top panel) and single Lambda DNA molecules after dUTP incorporation and glycosylase treatment creating abasic sites (bottom panel). The raw date (current traces) can be obtained as follows.

Thus, strand replication of a duplex molecule of Lambda DNA (DNA from Enterobacteria phage λ) by a DNA polymerase generates a copy of the original DNA strands which contain the four canonical bases A, C, G, T, and in random positions, have replacement of T with U (in the copy of the original DNA strand), (step B). The uracil-containing DNA is treated with UDG (uracil-DNA glycosylase) to produce abasic sites at positions of U incorporation into the DNA. Uracil DNA glycosylase enzyme is reacted with the polynucleotide to remove the uracil base, leaving the sugar phosphate backbone intact in the polynucleotide, but producing an abasic site at positions where the uracil had been incorporated into the DNA strand (Step D). In the panels of FIG. 3, raw data (nanopore current traces) from nanopore sequencing of DNA is shown in the top panel. Abasic sites (bottom panel) are identified by high current segments in the nanopore sequence data shown, where the horizontal line ("dotted line", bottom panel at about 90 pA) indicates current values in excess of those recorded for canonical DNA bases, i.e. current segments above the dotted line, mark positions of abasic sites. The current indicating an abasic site is increased above the current peaks observed for corresponding canonical bases and, in this example, peaks greater than about 90 pA. Current segments above the "dotted line" thus mark abasic positions within the polynucleotide sequence. The current traces shown in FIG. 3 (top and bottom panels) also show the location of a sequence loading adaptor and a hair pin adapter. These are oligonucleotides added to the DNA to be analyzed, according to a known nanopore protocol. These adaptors are used in preparation of the DNA before sequencing on the nanopore sequencer. The sequence loading adaptor is used in enzymatic loading of the DNA molecule into a nanopore for sequencing, and the hairpin adapter permits contiguous sequencing of both the template and complement strands by connection into a single strand, as illustrated schematically in FIGS. 7C and 7D. The raw data in FIG. 3 is interpreted by software specific for the nanopore-based sequencing device to generate a DNA sequence indicating the location of the abasic sites.

Figure 4A:
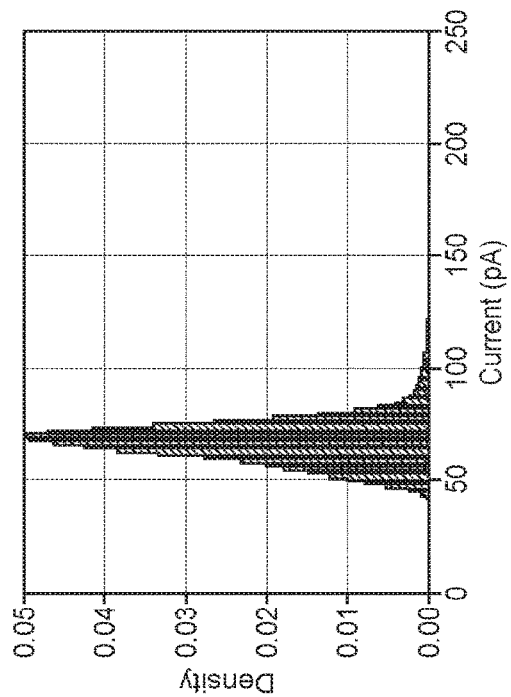
Figure 4C:
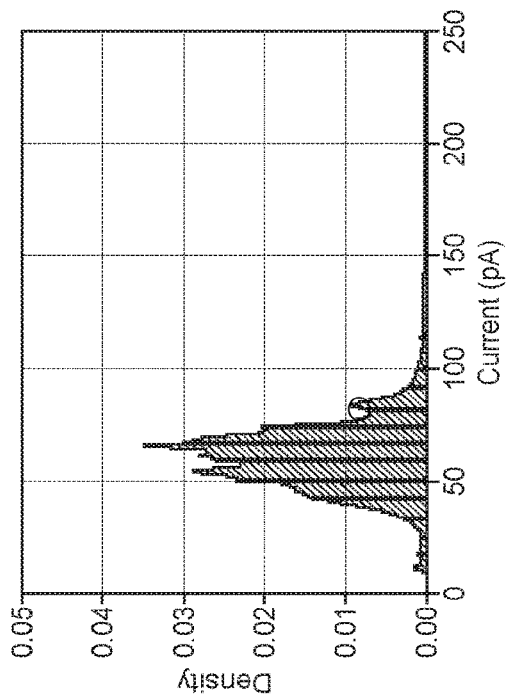
Figure 4B:
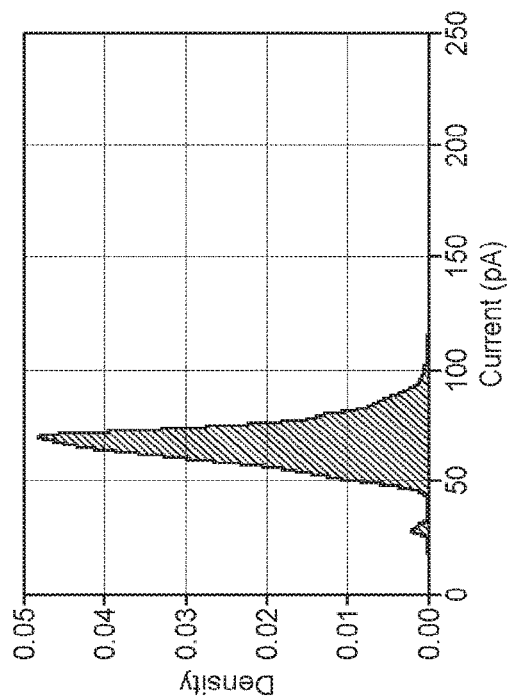

FIGS. 4A, 4B, 4C, and 4D is s series of graphs that show the distributions of mean currents (from 0 to 250 pA) for segmented current data used for base sequence determination in a nanopore sequencer (i.e. the MINION™ nanopore sequencer). Mean current levels derived from segmented current data, are characteristic of specific bases in a polynucleotide strand as they transit through the nanopore. These current levels sequentially change in a characteristic pattern determined by the sequence of the polynucleotide, and are used to determine DNA base sequence in nanopore sequencing. For the MINION™ nanopore sequencer, bases are processed through the nanopore sequentially one base at a time; however the sequencer detects 5 bases proximate to the aperture of the nanopore resulting in 1024 different current levels corresponding to all combinations of 5 bases. FIGS. 4A, 4B, 4C and 4D show the distribution of currents for 4 sequencing runs, one for each of 4 different populations of duplex Lambda DNA molecules from Enterobacteria phage k. The Y axis for FIG. 4A-4D is expressed as the percent of the total population of current segments from that sequencing run. FIG. 4A is the distribution of currents for Lambda DNA containing the 4 canonical bases. FIG. 4B is the distribution of current segments for Lambda DNA containing the 4 canonical bases (ACGT) and with Uracil substituted for T at random positions. FIG. 4C is the distribution of currents for Lambda DNA containing the 4 canonical bases then treated with DNA Uracil Glycosylase.

Figure 4D:
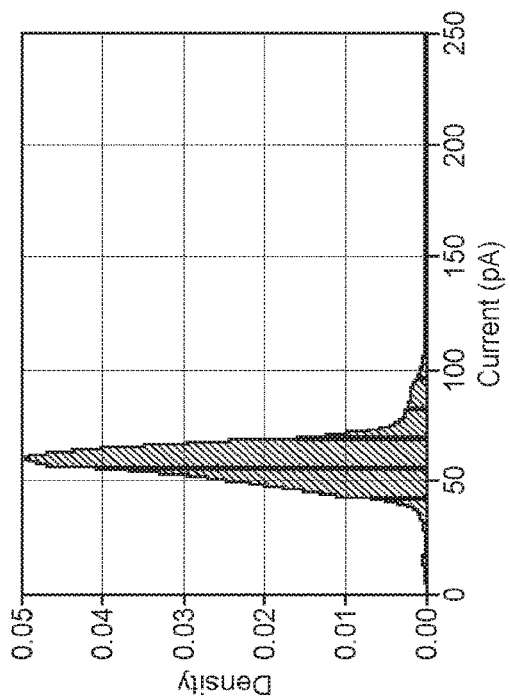

FIG. 4D is the distribution of currents for Lambda DNA containing the 4 canonical bases (ACGT) with Uracil substituted for T at random positions and treated with DNA Uracil Glycosylase. Abasic positions are associated with a high current relative to positions within a DNA strand that contain a canonical base. Only the density profile shown in 4D is expected to contain abasic sites. Note the peak at high current levels revealed as a spike on the shoulder of the current level distribution circled shown in the vicinity of 80 pA, and its absence in 4A, 4B and 4C. This is direct evidence of the detection of abasic positions in the polynucleotide populations examined.

Figure 5A:
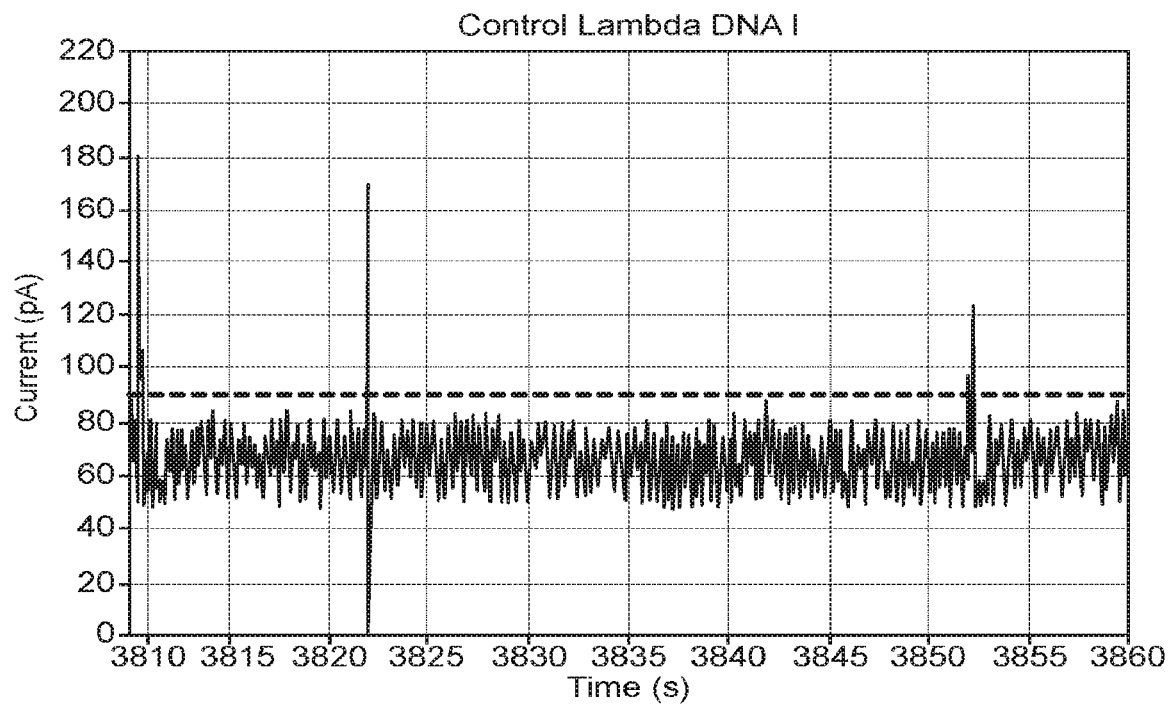
Figure 5B:
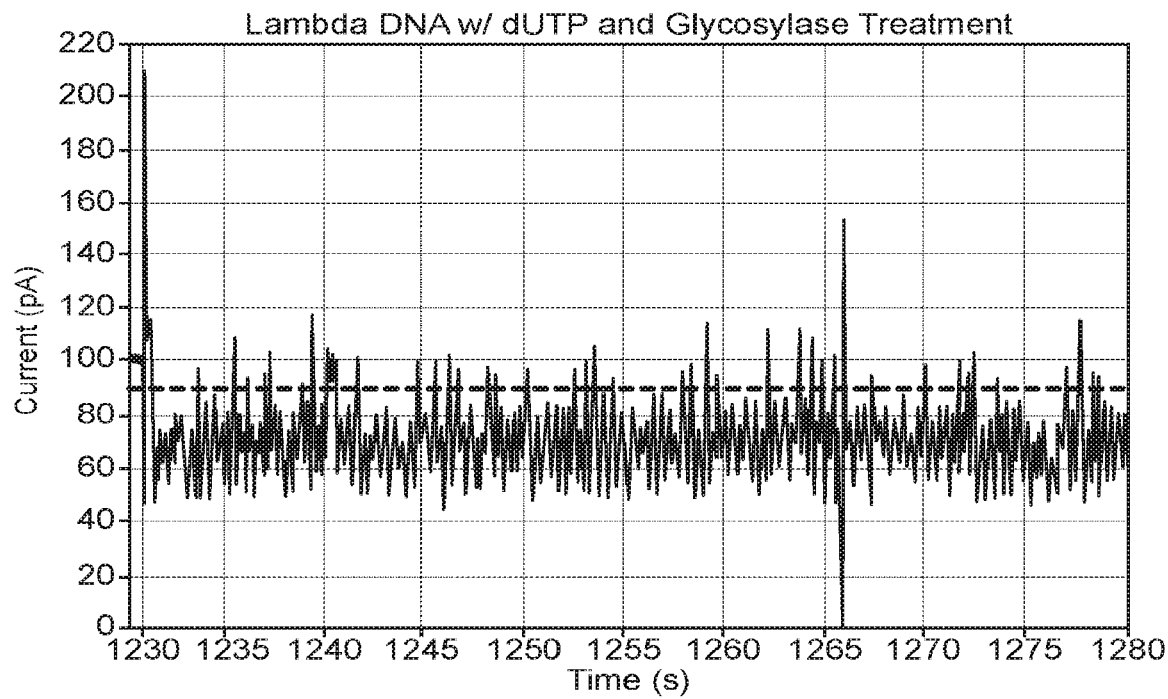

FIGS. 5A and 5B are a pair of current traces from control DNA and DNA where U bases have been removed by a uracil-DNA glycosylase. This figure shows MINION™ nanopore current data for a control DNA strand (5A) and abasic site containing DNA strand (FIG. 5B) obtained from nanopore sequencing runs. Comparison of control Lambda DNA (5A) and glycosylase treated DNA (5B) shows current spikes above the reference line (dotted line) at about 90 pA shown in FIGS. 5A and 5B. The current segments above 90 pA are from abasic sites created by removal of uracil from the polynucleotide by uracil-DNA glycosylase.

Figure 6:
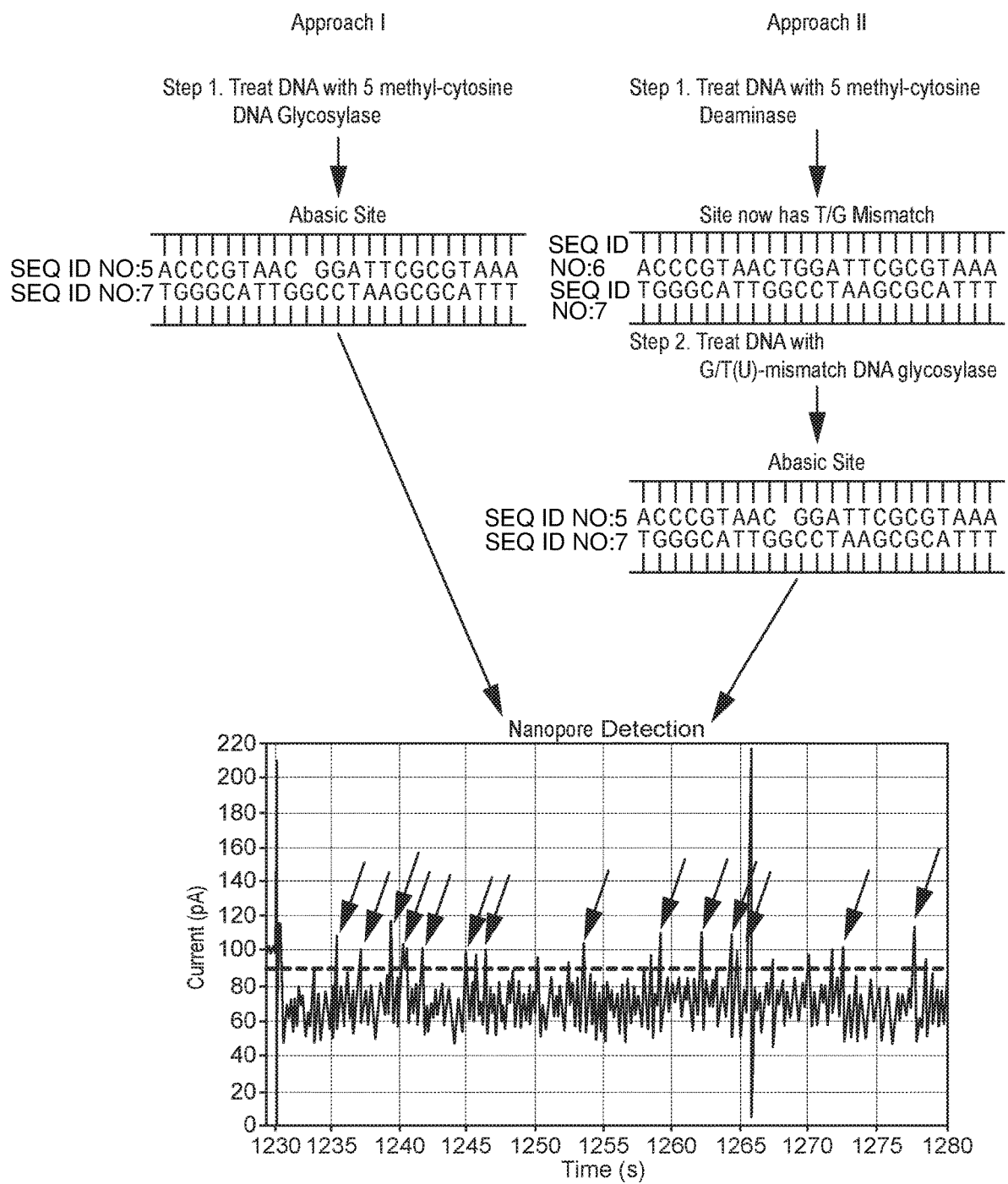

FIG. 6 is a schematic diagram that shows two approaches to a procedure for detecting high current signals at abasic sites (arrows at bottom panel) in a nanopore (MINION™) sequencing device. Abasic sites are those where C5-methylcytosine, having been prepared with a G base on an opposite strand, are removed, thereby identifying the C5-methylcytosine in the sample. In Approach I, a representative dsDNA molecule containing a C5-methylcytosine at a random location is treated with 5 methyl-cytosine DNA glycosylase to produce an abasic site. In approach II, a molecule such as in Approach I is treated with 5 methyl-cytosine deaminase to convert the C5-methylcytosine to a T, creating a T/G mismatch. This molecule is then treated with G/T(U)-mismatch DNA glycosylase to create the desired abasic site. As shown in the bottom panel, high current signals at abasic sites can be detected by increased current.

Figure 7A:
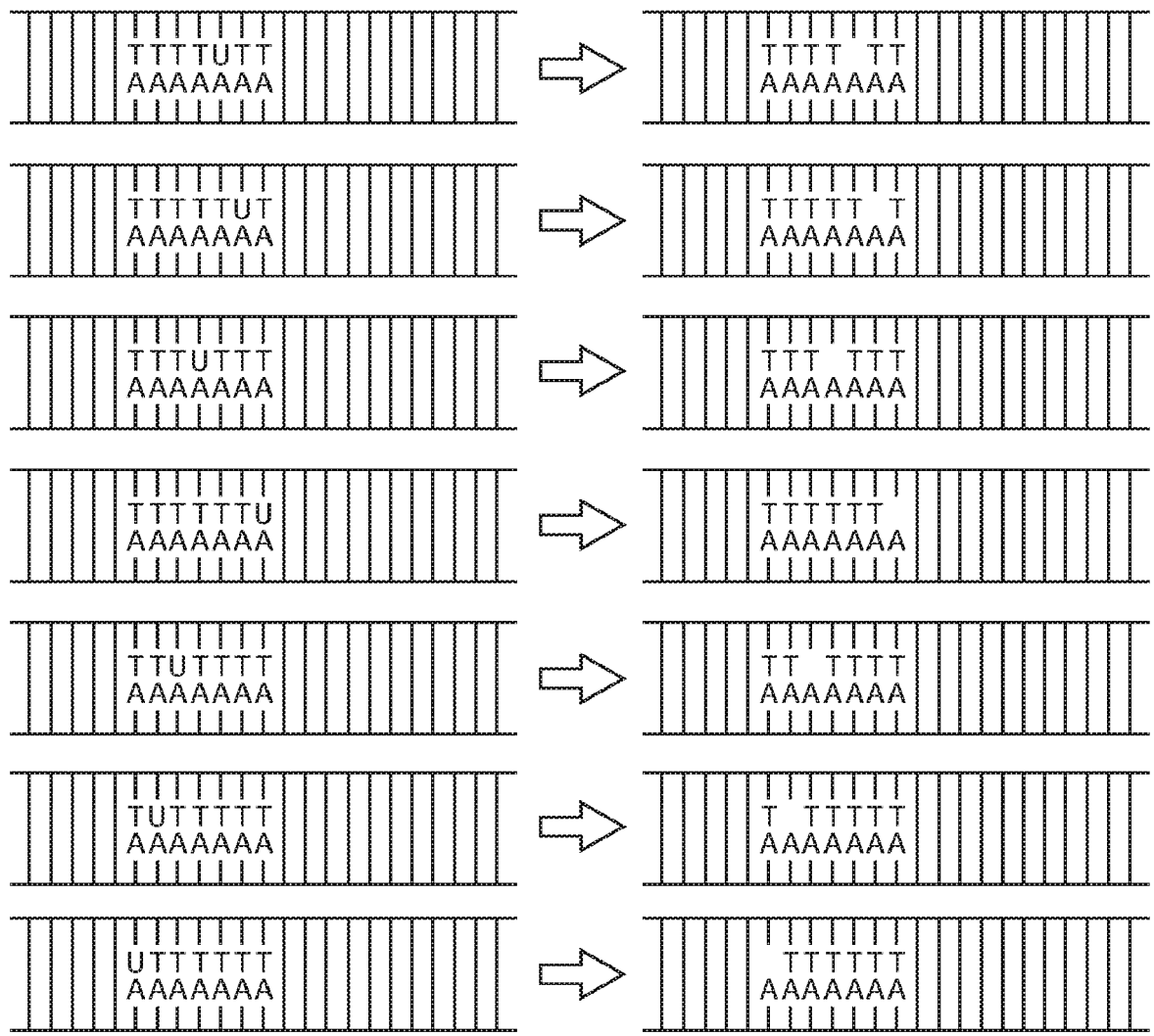

FIG. 7A is a schematic representation of a process to improve the accuracy of homopolymeric runs of T's and A's in a DNA molecule being sequenced. In a first step, DNA polymerase and a mixture containing U is used to replace a fraction of T's in the sequence with U's, giving DNA duplexes such as shown on the left of the figure. In a second step, uracil DNA glycosylase is reacted with the product of the first step and used to create abasic sites, giving DNA duplexes such as shown on the right of the figure. Then, the abasic sites are identified as described above, using nanopore-based sequencing. The abasic site-containing sequences obtained are aligned using bioinformatics tools. Positions of abasic sites in the alignment are determined and counted. 5mers with altered current profiles due to abasic positions within the 5mer are determined. This information is used to determine the length of the homopolymeric run of T's. Alternatively a DNA glycosylase engineered to remove T can be used to effect the same analysis in fewer enzymatic steps.

Figure 7B:
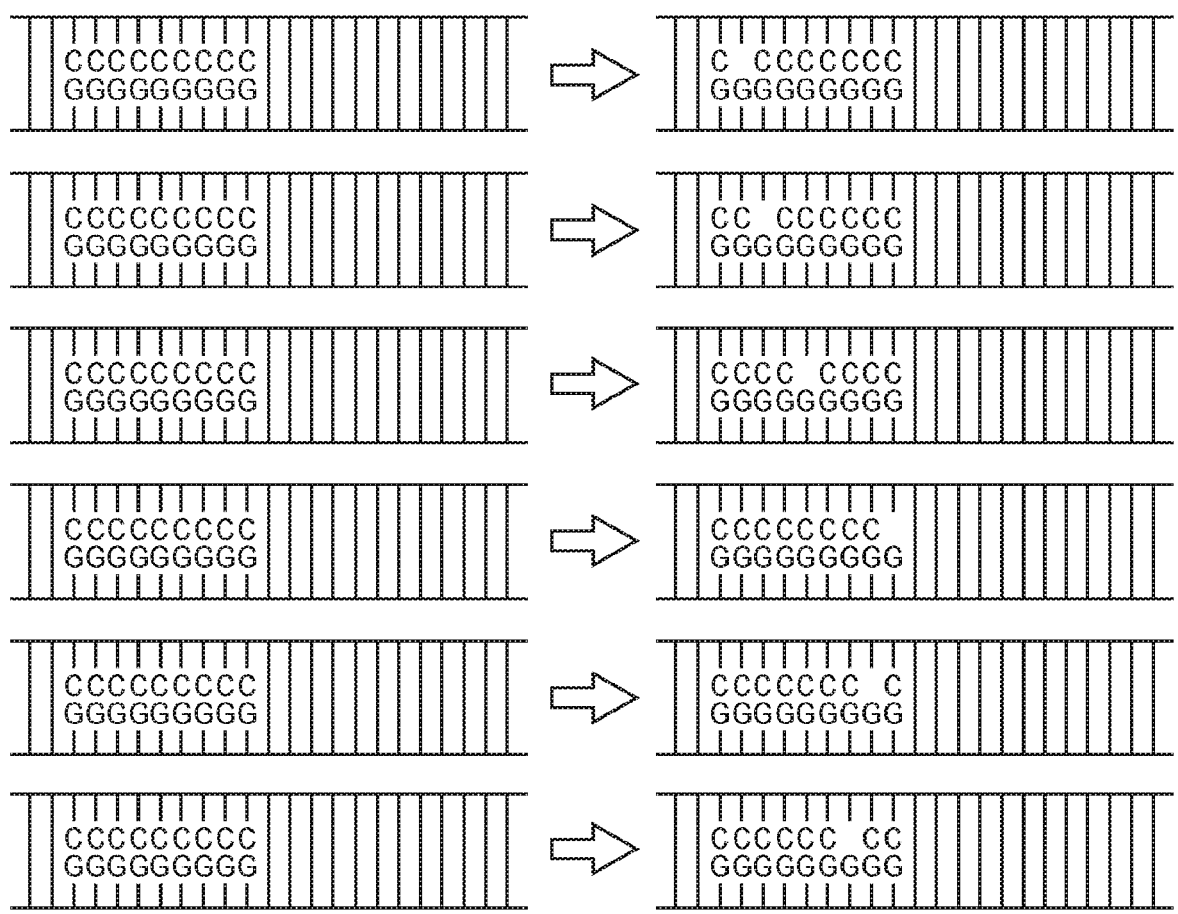

FIG. 7B shows an approach for detecting repetitive (homopolymeric) sequences of C. Using a DNA glycosylase engineered to remove C, a similar analysis to that for homopolymeric tracks of T can be completed for homopolymeric tracts of C.

Figure 7C:
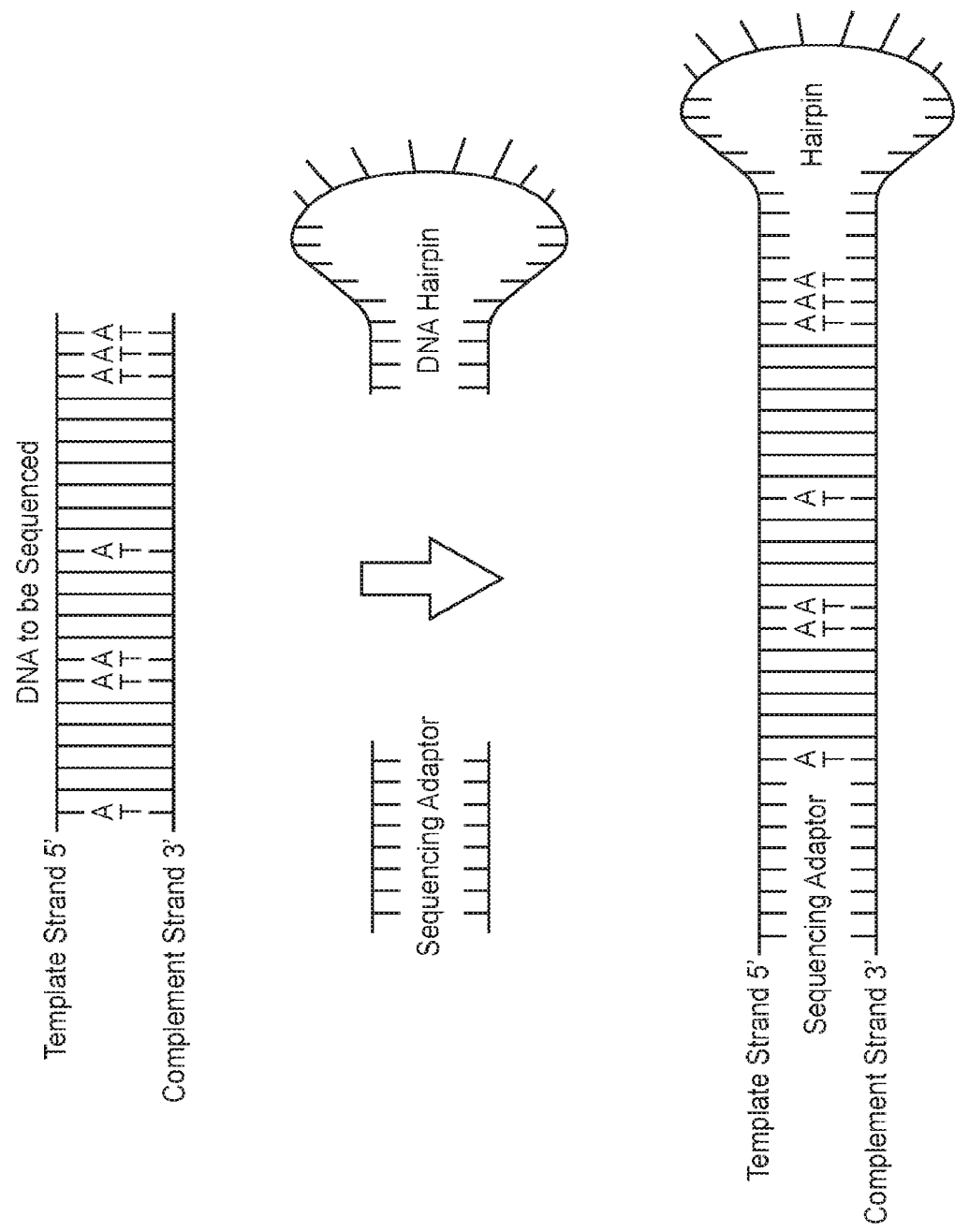
Figure 7D:
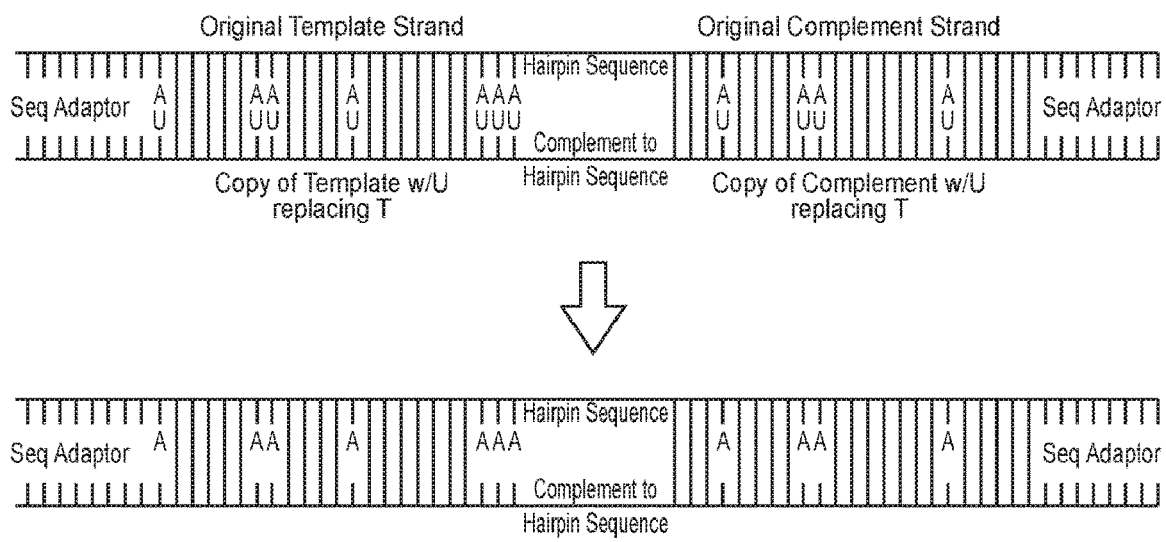
Figure 7D:
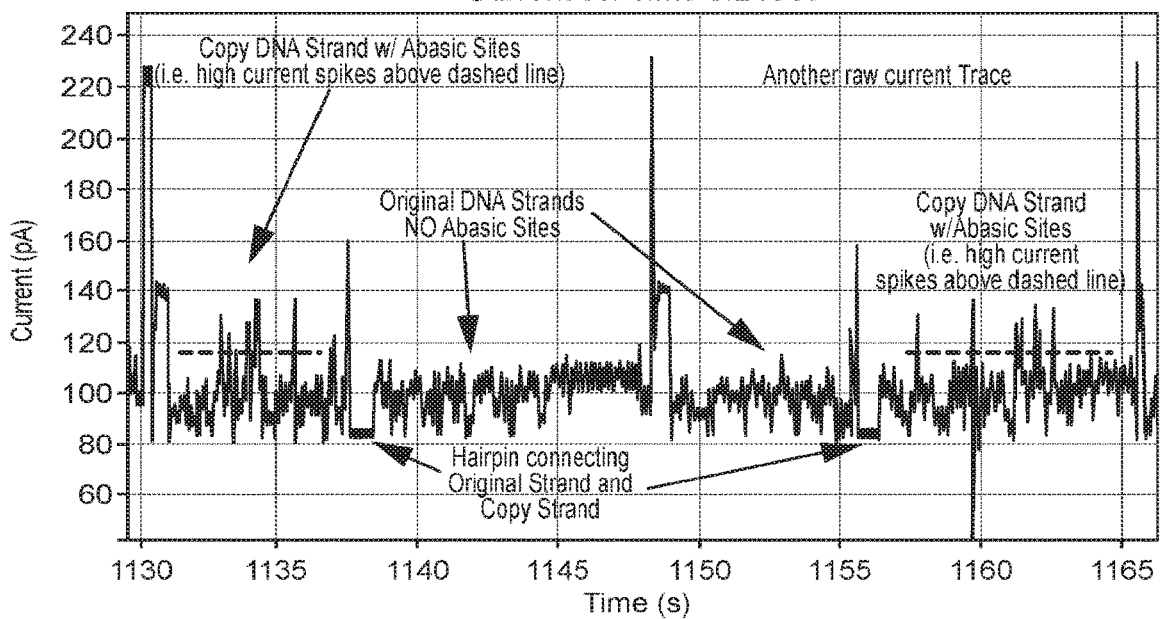

FIG. 7C, 7D shows an approach for detecting certain bases that can be replaced with bases that are glycosylase substrates. Also shown is a dsDNA prepared with a hairpin to enable individual sequencing of both strands of the dsDNA.

Figure 8:
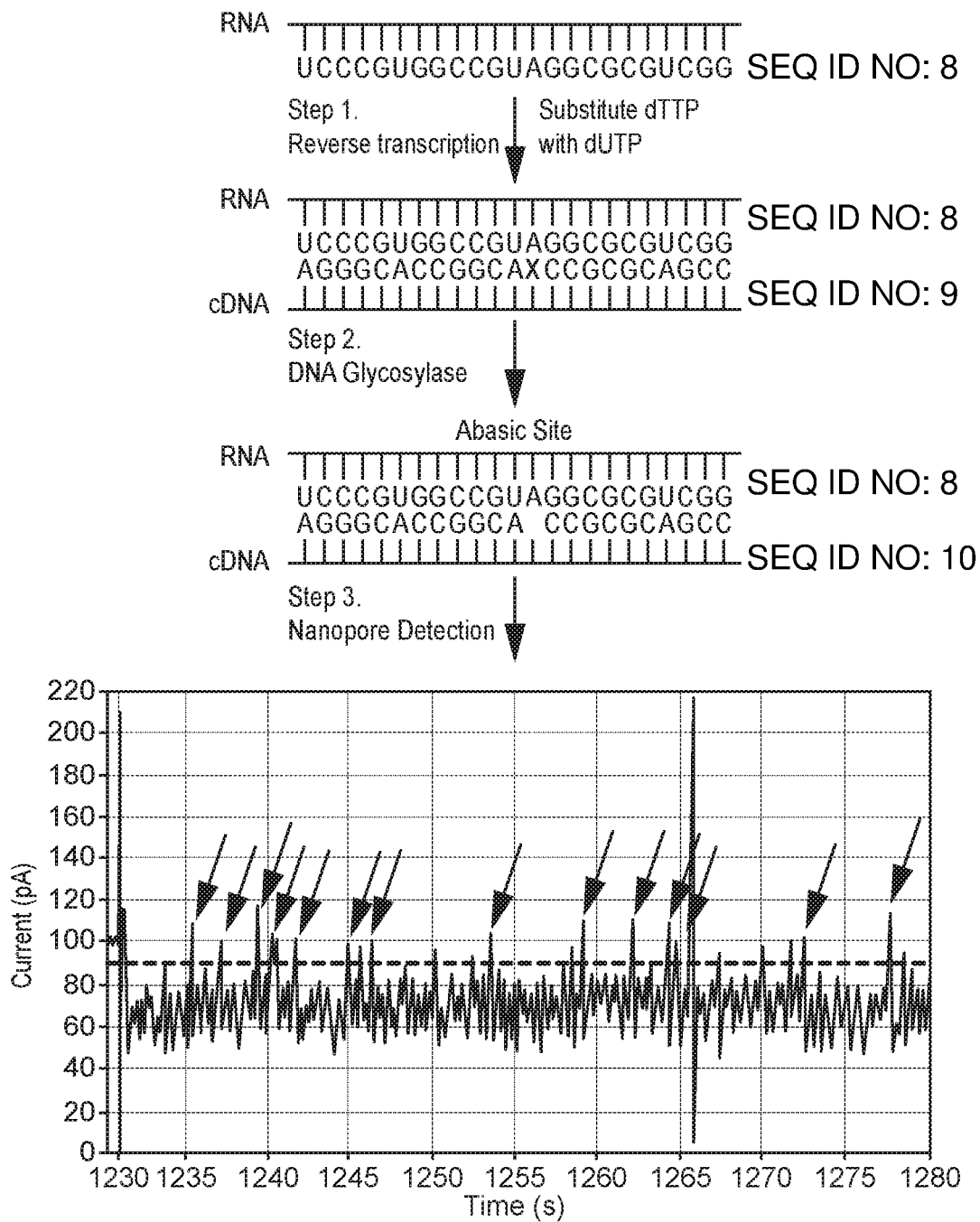

FIG. 8 is a schematic diagram that shows an improved method of sequencing RNA using the present method, where abasic sites are created. In step 1, reverse transcriptase is used to create a DNA-RNA heteroduplex. The provided nucleotides for polymerization include U to be incorporated complementary to the A in the RNA. In step 2, DNA glycosylase is used to remove the U residues inserted in step 1, e.g. with uracil DNA glycosylase, to create abasic sites that are detected in step 3 by a MINION™ nanopore-based sequencing device.

Figure 9:
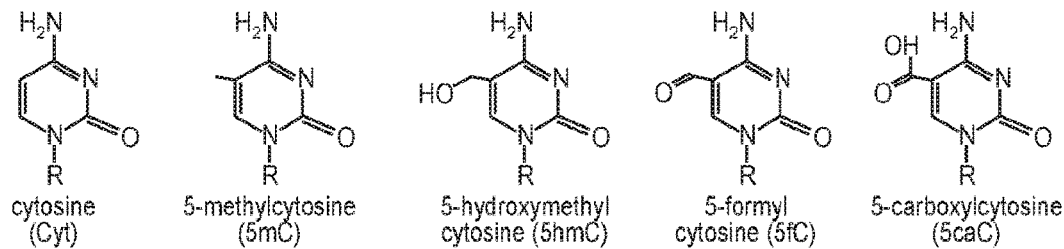

FIG. 9 shows structures of cytosine and modified cytosines, which are the subject of a process for a combination of different enzymatic treatments of a polynucleotide that will detect different base modifications in a single sequence in a sample, as described below. The method detects and distinguishes cytosine, 5-methylcytosine, 5-hydroxy cytosine, 5-formyl cytosine and 5-carboxycytosine. In each case the cytosine species is treated with a glycosylase specific for Cyt or the non-canonical base of interest (5mC, 5HmC, 5fC, or 5caC) to generate an abasic site at the specific location of the species of interest. If an appropriate glycosylase is available, a two-step process is carried out. Alternatively, in the first step, the cytosine species is enzymatically converted to another base that can be removed to form the abasic site.

Figure 10:
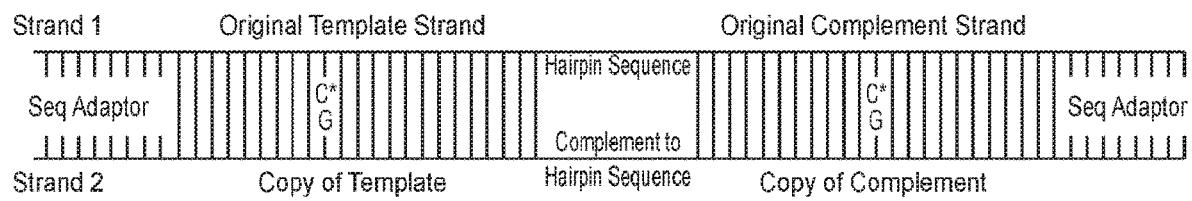
Figure 10:
Figure 10:
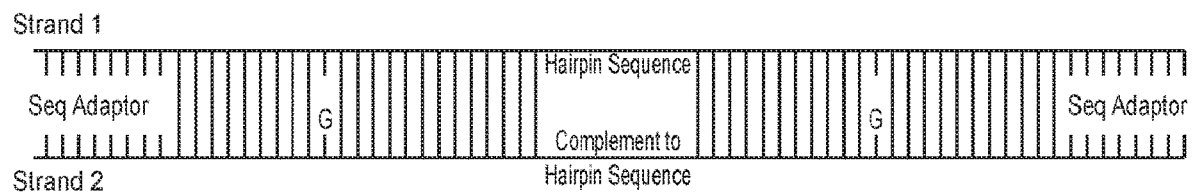

FIG. 10 is a schematic representation of a sequencing process wherein modified bases are detected by preparation of a complementary strand to the template strand. The complementary strand is prepared with the canonical bases. The modified bases are excised as described above, and the sequence will have information both of the abasic site and the complement of the original modified base.

DETAILED DESCRIPTION

Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well-known and commonly used in the art. Certain experimental techniques, not specifically defined, are generally performed according to conventional methods well known in the art and as described in various general and more specific references that are cited and discussed throughout the present specification. For purposes of clarity, the following terms are defined below.

Ranges: For conciseness, any range set forth is intended to include any sub-range within the stated range, unless otherwise stated. As a non-limiting example, a range of 120 to 250 is intended to include a range of 120-121, 120-130, 200-225, 121-250 etc. The term "about" has its ordinary meaning of approximately and may be determined in context by experimental variability. In case of doubt, the term "about" means plus or minus 5% of a stated numerical value.

The term "abasic" or "abasic site" is used in its conventional sense. An abasic site is also known as an AP site, or apurinic or apyrimidinic site. In a DNA or RNA strand, an abasic site is one in which the base is not present, but the sugar phosphate backbone remains intact. Abasic sites may exist in various tautomeric forms within a polynucleotide. For details, see Krotz et al., U.S. Pat. No. 6,586,586, "Purification of Oligonucleotides," issued Jul. 1, 2003. As described there, an abasic site may comprise a mixture of four chemical species in a tautomeric equilibrium. For example, an abasic site can be an apurinic or apyrimidinic site located on an oligonucleotide, wherein an aldehyde moiety is present. For example, this is shown in FIG. 4 of U.S. Pat. No. 6,586,586.

The term "modified base" refers to a nucleobase in a polynucleotide (DNA or RNA) which is not one of the 5 canonical standard bases, i.e. A, C, G, and T and, in RNA, U. U (uracil) may be regarded as a modified base in DNA and a canonical base in RNA. Using conventional notation, in all sequences here, "A" stands for adenine. "G" stands for guanine, "C" for cytosine, and "T" for thymine. Adenine always pairs with thymine. Cytosine always pairs with guanine.

The term "predetermined nucleobase species" accordingly refers to a selected species such as A, C, G, T, or U as canonical base sequences, or a species that is modified as described herein, such as methyl cytosine (e.g. 5-methyl cytosine), 5-fluorouracil, 3-methyladenine, 5-carboxycytosine, 8-oxoguanine, etc. as set forth further in Table 1.

The term "polynucleotide" is used in its conventional sense to include polynucleotides that are human DNA, human RNA, human cDNA and counterparts in other organisms including plants, microorganisms and viruses. The polynucleotides used here typically comprise two strands of a DNA molecule that occur in an antiparallel orientation, where one strand is positioned in the 5' to 3' direction, and the other strand is positioned in the 3' to 5' direction. The terms 5' and 3', as is conventional, refer to the directionality of the DNA backbone, and are critical to describing the order of the bases. The convention for describing base order in a DNA sequence uses the 5' to 3' direction, and is written from left to right. The term polynucleotide includes oligonucleotides, and in general, is formed from a plurality of joined nucleotide units, including linear sequences of nucleotides, in which the 5' linked phosphate or other internucleotide linkage on one sugar group is covalently linked to either the 2'-, 3'-, or 4'-position on the adjacent sugars. Also included within the definition of polynucleotide as an "oligonucleotide" are other double stranded oligonucleotides including DNA, RNA and plasmids, vectors and the like. Thus, the term "oligonucleotide" includes linear sequences having 2 or more nucleotides, and any variety of natural and non-natural constituents as described below.

The term "reference sequence" refers to a known sequence that corresponds to a sequence obtained during a sequencing method being carried out. A sequence corresponds to a sequence of interest if it may be presumed to have a high degree of sequence identity (>90%) to the sequence under study within the region of interest. A reference sequence may be a sequence determined by sequencing a nucleotide in the same sample as a sequence under study, or it may be a sequence obtained from a database of known sequences. A reference sequence may be obtained by comparison to, for example, the obtained from the UCSC Genome Browser.

The term "nanopore-based sequencing", as used herein, means a process for determining the order in which specific nucleotides occur on a strand of polynucleotide, based on a physical interrogation of monomers in a single strand at a time. Individual monomers may be identified one-by-one, in unique groups (e.g. 5mer), or otherwise uniquely identified by their structural characteristics.

The term "nanopore-based sequencing method" further refers to use of a physical structure in the form of a nanopore or equivalent structure. A nanopore itself is simply a small hole, of the order of 1 nanometer in internal diameter, through a thin film through which a polynucleotide being sequenced passes. The theory behind nanopore sequencing is that when a nanopore is immersed in a conducting fluid and a potential (voltage) is applied across it, an electric current due to conduction of ions through the nanopore can be observed. Nanopore sequencing devices are described, e.g. in Schneider & Decker, "DNA Sequencing with nanopores," Nature Biotech. 30 326-328 (2012), which is incorporated for further descriptions of nanopore systems, enzymes and pores used. See also Akeson et al. "Methods and apparatus for characterizing polynucleotides," U.S. Pat. No. 7,238,485; Peng et al., "Electron beam sculpting of tunneling junction for nanopore DNA sequencing," U.S. Pat. No. 8,858,764; and Ju "DNA sequencing by nanopore using modified nucleotides," U.S. Pat. No. 8,889,348. In connection with the latter patent, it will be described herein that the modifications of specific, pre-selected bases are carried out and distinguished from the canonical bases. An enzyme (e.g. a DNA polymerase or other transposase) is used to modulate the passage of the polynucleotide through the nanopore).

As also described in the preceding referenced patent, the present methods may also detect an electronic signature, where an "electronic signature" of a nucleotide passing through a pore via application of an electronic field shall include, for example, the duration of the nucleotide's passage through the pore together with the observed amplitude of current during that passage. Electronic signatures can be visualized, for example, by a plot of current (e.g. pA) versus time. Electronic signature for a DNA is also envisioned and can be, for example, a plot of current (e.g. pA "picoamperes") versus time for the DNA to pass through the pore via application of an electric field.

Another embodiment of nanopore sequencing is nanopore sequencing with current detection or optical detection, physical molecule (magnetic) extension (Ding et al. "Single-molecule mechanical identification and sequencing, Nature Methods 9, 367-372 (2012).

Nanopore-based sequencing may, in some embodiments, employ a base-by-base interrogation of a single polynucleotide molecule. Methods have been used for nanopore physically based sequencing that use, for example, electron tunneling. Measurement of electron tunneling through bases as ssDNA translocates through the nanopore may be used. Most research has focused on proving bases could be determined using electron tunneling. These studies were conducted using a scanning probe microscope as the sensing electrode, and have proved that bases can be identified by specific tunneling currents (Chang, S; Huang, S; He, J; Liang, F; Zhang, P; Li, S; Chen, X; Sankey, O; Lindsay, S (2010). "Electronic signatures of all four DNA nucleosides in a tunneling gap". Nano Lett. 10: 1070-1075).

In the present nanopore-based sequencing, no labelling of the nucleotides or biologic functionality is required to determine the sequence during the nanopore base sequencing step. The term "nanopore-based sequencing method" includes, but is not limited to, "nanopore sequencing," which is a nanopore-based sequencing method exemplified herein.

The term "RNA glycosylase" refers to an enzyme that catalyzes the hydrolysis of N-glycosylatic bonds in an RNA molecule. This includes EC 3.2.2.22. The references here to DNA glycosylases may be used to employ RNA glycosylases for RNA.

The term "DNA glycosylase" refers to a family of enzymes that remove bases from DNA. Typically such enzymes are involved in base excision repair, classified under EC number EC 3.2.2. Based on structural similarity, glycosylases are grouped into six structural superfamilies. The UDG and AAG families contain small, compact glycosylases, whereas the MutM/Fpg and HhH-GPD families comprise larger enzymes with multiple domains.

Another DNA glycosylase used here is uracil-DNA glycosylase, which excises uracil from dU-containing DNA by cleaving the N-glycosidic bond between the uracil base and the sugar backbone. This cleavage generates alkali sensitive apyrimidinic sites that are blocked from replication by DNA polymerase or prevented from becoming a hybridization site. This glycosylase is also referred to here for convenience as a DNA glycosylase.

Alternative glycosylases used here include glycosylase enzymes engineered to remove beta-lyase activity for the purpose of using the glycosylase to create abasic sites for detection of modified bases with a nanopore DNA sequencer.

Alternative glycosylases useful here include glycosylase enzymes engineered to have altered base specificity for the purpose of using the glycosylase to create abasic sites for improvement of nanopore DNA sequencer accuracy and performance. Examples modified human uracil DNA glycosylase (Gene Symbol UNG) include conversion of Tyr147 to Ala147, resulting in activity of the glycosylase cleaving both uracil and thymine. Similarly, changing Asn204 to Asp204 results in this glycosylase cleaving both uracil and cytosine. For details, see Kavli, B; Slupphaug, G; Mol, C D; et al. "Excision of cytosine and thymine from DNA by mutants of human uracil-DNA glycosylase," EMBO JOURNAL Volume: 15 Issue: 13 Pages: 3442-3447 Published: Jul. 1, 1996.

The term "epigenetic modification" is used to refer to an alteration in a DNA sequence that changes a base in the sequence from a canonical Base to another chemical species. Examples include 5-methyl cytosine, 5-hydroxymethyl cytosine, 5-formyl cytosine, 5-carboxy cytosine, etc.

The term "single molecule sequencing" refers to a sequencing method that is not carried out on a population of molecules amplified from a sample. Several art-recognized methods of single-molecule sequencing have been developed (see U.S. patent application US2006000400730 and U.S. Pat. Nos. 7,169,560; 6,221,592; 6,905,586; 6,524,829; 6,242,193; 6,221,592; and 6,136,543. Commercial examples include the Oxford Nanopore Technology MINION™ and GRIDION™ devices, the Helicos Biosciences Corporation HELISCOPE™, the SMRT sequencing method from Pacific Biosciences of California, Inc., etc.

General Method and Apparatus

Figure 1A:
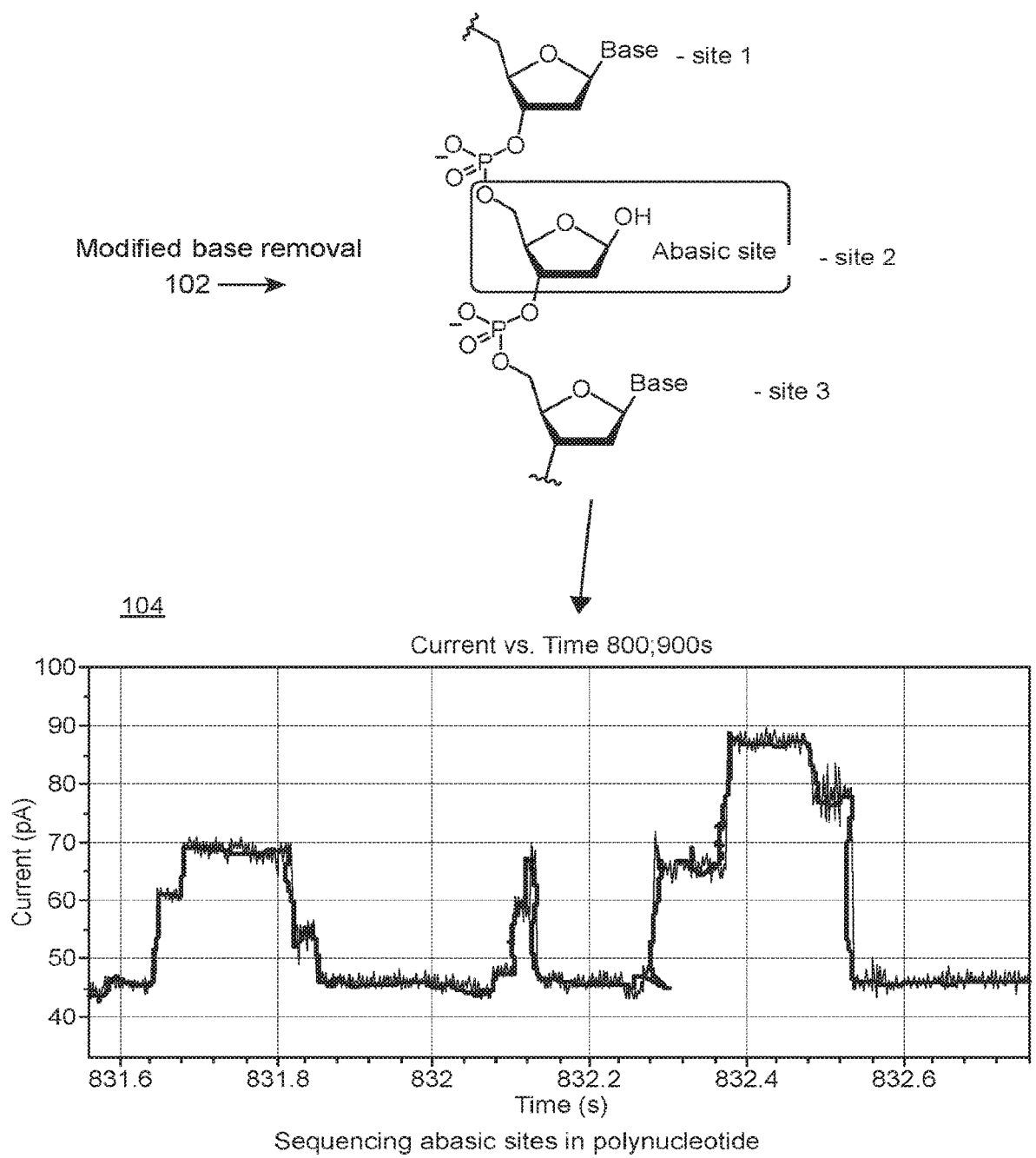
FIG. 1A, 1B is a schematic diagram and a set of traces, respectively, illustrating the process of sequencing a polynucleotide using abasic sites.

The present nanopore-based sequencing process is preferably carried out in a high-throughput device, and employs computer technology to measure the physical parameters associated with translocation of the bases in a polynucleotide through a nanopore, e.g. ionic current blockade as bases occlude the nanopore during translocation. As is known, the device will contain logic devices for analyzing the raw sequence and matching it to specific bases in a sequence. As explained below, an important physical characteristic of abasic sites is the lack of a base in a moiety in the polynucleotide, as shown in FIG. 1A.

Detection of polynucleotide base sequence with the presently exemplified nanopore sequencing relies on detection of changes in ionic current as a polynucleotide passes through the nanopore. The electrical signature (ionic current) from an abasic site passing through a nanopore is increased and distinguishable from any base-containing site. It is understood that the polynucleotide used in the nanopore physically based sequencing will be prepared for sequencing by various processes, and will be acted upon by various chemical or biological agents, such as enzymes controlling translocation of the polynucleotide, but the detection system makes the distinction shown in FIG. 1A by directly detecting the nature of the bases, and particularly the lack of a base. The present methods may be used with existing sequencing hardware and software, and the sequence signal obtained can be interpreted by software routines that call the nucleotide at sites 1 and 3 as per preprogrammed base calling, and also recognize site 2 as abasic. A schematic representation of a sequence signal is shown at the bottom of FIG. 1A. Although site 2 here is a distinctly higher peak, alternative hardware and software could characterize site 2 in other ways to distinguish it from canonical bases at site 1 and site 3. Nanopore electrical current signals from abasic sites (no base, but intact sugar phosphate backbone) within DNA strands are significantly different from electrical current signals for adenine, cytosine, guanine and thymine bases, as well as modified bases, and are reliably detected. This invention determines the specific location of a modified DNA base e.g. 5-methylcytosine (mC) by using modified base specific DNA glycosylases to create abasic sites within DNA duplex molecules at the site of the modified base. The newly created abasic positions within the DNA strand are then detected by a nanopore sequencer such as the MinION™ nanopore sequencer with high precision and recall. This invention can be used to detect a wide spectrum of modified DNA and RNA bases as well as improve sequencing accuracy. Applications of this invention include epigenetic sequencing with the MinION or other nanopore sequencer and detection of cancer chemotherapeutic agents, chemical mutagens and carcinogens bound to DNA.

The present methods comprise selecting the modified base (or set of bases) that will be determined in a particular embodiment. If there is a modified base in a sequence (e.g. DNA double helix), one first determines if the modified base to be detected is a known and specific substrate for a glycosylase. If it is, the modified base (in the polynucleotide strand being characterized) is treated directly with the appropriate glycosylase to generate abasic sites where the modified base was located in the strand. The present methods may comprise a preparation where a polynucleotide, e.g. cDNA, genomic DNA, mRNA, genomic RNA, etc., may be analyzed for the presence of a subset of bases. The bases of interest may be modified bases (i.e. modifications of canonical A, T, C, G, or U) wherein the modified base of interest is present in the polynucleotide in the form of a substrate for a glycosylase. If the modified base of interest is not a substrate for a known glycosylase, the modified base is treated to convert it into a nucleobase that is a substrate to a known glycosylase. That is, it may be treated by a base-specific base modification enzyme, or treated by chemical conversion, etc. so as to produce an appropriate substrate. After the desired abasic sites are created, one carries out nanopore physically based sequencing, which will, as described below, generate a readily determined signal at the point in the sequence where the abasic sites exist.

In another embodiment, one may determine epigenetic modified cytosines in genomic DNA. If the modified base is 5-methylcytosine, which is a glycosylase substrate, one treats the DNA of interest with 5-methylcytosine glycosylase, causing removal of 5-methylcytosines from the sequence and leaving abasic sites in its place. Determination of the sequence and detection of the created abasic sites is carried out, again using nanopore physically based sequencing (e.g. MinION™ mobile DNA sequencer). Alternatively, or additionally, if one wishes to determine the presence of 5-hydroxymethylcytosine bases in the sequence, one can treat the sample with KRuO4 to convert the 5-hydroxymethylcytosine bases to 5-formylcytosine. Then, the sample may be treated with thymine DNA glycosylase to produce abasic sites at the bases of interest. Again the abasic sites are readily determined as to their location in the sequence of the sample, as described below, namely with current spikes higher than that generated by base-containing residues.

As will be described below, the present invention is a broadly applicable method for sequence specific detection of modified bases. Applications of the present methods include identification of epigenetic markers on cytosine; improvement of nanopore sequencing accuracy; biological monitoring of chemotherapeutic drugs; biological monitoring of environmental carcinogens, and so forth.

Figure 2:
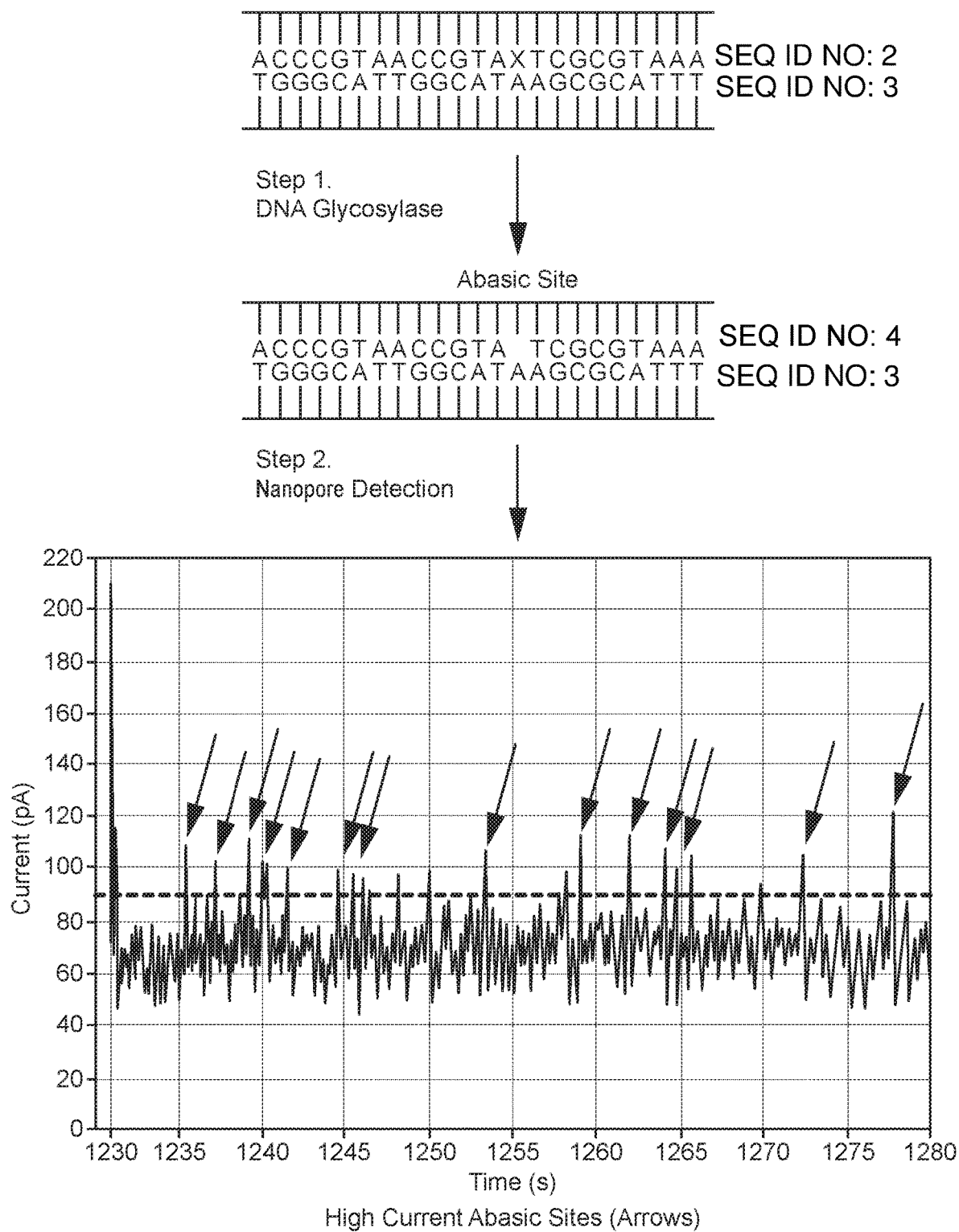
FIG. 2 is a schematic diagram showing steps that illustrate embodiments of the present process using a double stranded DNA with a polynucleotide having standard nucleobases A, T, G, C, and a non-standard base X, which may be as listed here, or in Table 1. X may include epigenetic markers on genomic DNA (e.g. C5-methylcytosine or mC) and various forms of DNA damage, including DNA adducts (drugs or carcinogenic pollutants), mitochondrial genome damage (8-oxo-guanine), base analogs (AIDS and anti-cancer drugs), UV damaged DNA (thymine dimers), and ethenolated bases that include: $1,N^6$-alpha-hydroxyethenoadenine; $1,N^6$-ethenoadenine; $3,N^4$-ethenocytosine; $1,N^2$-ethenoguanine; and $N^2,3$-ethenoguanine.

Examples are given here of experiments that generated a set of abasic sites in DNA at positions of T within the DNA strand. This DNA was then sequenced in the MinION Nanopore Sequencer and data analyzed for the presence of abasic sites. See FIG. 2 for an outline of the use of DNA glycosylases to create and detect abasic sites at predetermined points within a sequence. Similarly, FIG. 3 shows nanopore sequencing data obtained from Lambda phage DNA. The experimental details are given below.

Example 1A: Preparation of Modified and Abasic Polynucleotides

1. A 3.7 kb fragment of Lambda phage was amplified using PCR. PCR reactions were run under two conditions, a control (canonical dNTPs) and a PCR reaction that included the 4 canonical dNTPs plus dUTP.
2. The PCR products were purified, re-suspended in high purity water and quantified on a Nanodrop UV/VIS spectrophotometer. Two hundred nanograms of PCR products were run on a 0.8% agarose gel to confirm size and purity.
3. Two aliquots of 2 ug each, one from the control canonical dNTPs PCR reaction and one from the dUTP PCR reactions, were used to prepare sequencing libraries using ONT (Oxford Nanopore Technologies) standard procedures (ONT library preparation procedure 004).
4. One aliquot from each PCR reaction was treated for 15 min with Uracil-DNA glycosylase and bead purification immediately after end repair in the library preparation process. This resulted in the generation of 4 samples for sequencing. The 4 reactions have the following compositions.
   a. Control i.e. 3.7 kb lambda fragment containing canonical bases ACGT, and no abasic sites
   b. Control i.e. 3.7 kb lambda fragment containing canonical bases ACGT and Uracil-DNA glycosylase treatment, with no abasic sites.
   c. Uracil PCR reaction containing 3.7 kb lambda fragment containing canonical bases ACGT plus uracil, with no abasic sites.
   d. Uracil PCR reaction containing 3.7 kb lambda fragment containing canonical bases ACGT plus uracil which was treated with Uracil-DNA glycosylase. Contains abasic sites at sequence positions with incorporation of dUTP.

Example 1B: Sequence Analysis Including Abasic Sites and Sequence Coverage

Figure 1B:
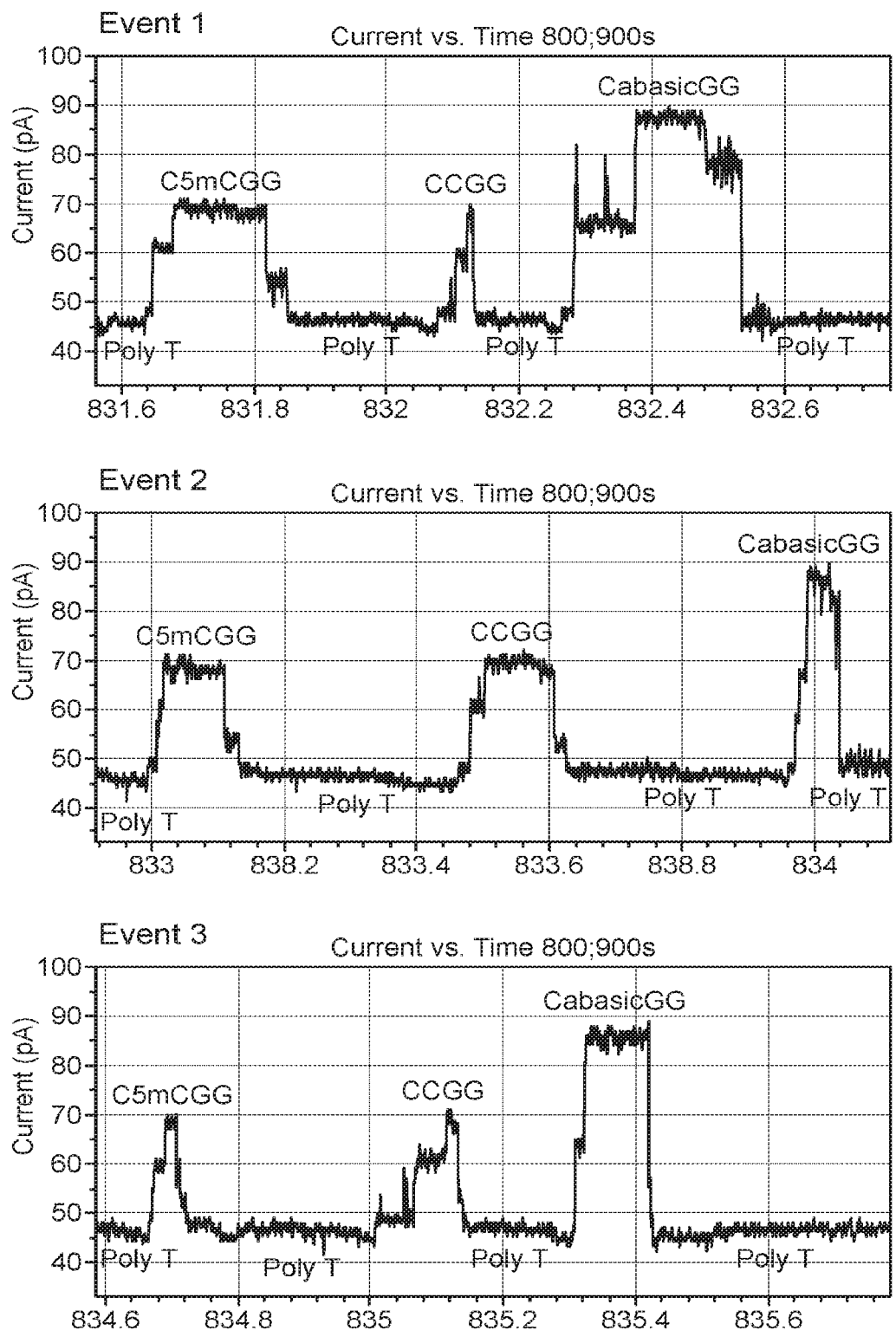

Abasic sites in a polynucleotide are created at specific base locations, as described above. The polynucleotide, containing canonical bases and abasic sites, is then sequenced in a nanopore-based sequencing device. As is known, such a device can produce ionic current traces corresponding to translocation of a DNA strand through the nanopore; these can be divided into segments of ionic current, where the mean and variance in current for each segment depends on the identity of the bases proximal to the "reading head" of the nanopore. The "reading head" of the nanopore includes both the limiting aperture and adjacent areas of the nanopore where bases in the polynucleotide can interact with the nanopore to alter ionic current through the nanopore. The first step in analyzing a current trace (shown e.g. in FIG. 1B) is to segment it, using appropriate electronics and software. Five to five hundred segments per second are generated by the segmentation software analyzing the raw ionic current signal. The number of segments per unit time depends on the speed of the DNA motor (enzyme) modulating translocation of the DNA/polynucleotide through the nanopore.

The next step in data analysis after segmenting an ionic current trace is to determine which bases are present at the reading head of the nanopore for each ionic current segment. Currently for the MinION™ nanopore sequencer, these ionic current segments depend on the 5 contiguous bases proximal to the reading head of the nanopore. A lookup table containing all 1024 possible combinations of 5 bases is used to identify these 5 base long blocks or 'words' for sequence determination as they translocate through the nanopore. That is to say, the polynucleotide is detected by the nanopore as 5 base long words that move through the nanopore in 1 base steps. Accordingly, a single base position alters ionic current when it is within 5 bases or less of the reading head of the nanopore. Additionally each base position in a polynucleotide influences 5 contiguous ionic current segments. For analysis of the polynucleotides of canonical base sequence, hidden Markov models (HMMs) based software is used to translate information from segmented current data into DNA sequences. An exemplary hidden Markov Model is further described in Sjolender, "Method and apparatus using Bayesian subfamily identification for sequence analysis," U.S. Pat. No. 6,128,587. HMMs can be constructed to identify sets of positions that describe the (more or less) conserved first-order structure in a set of sequences. In biological terms, this corresponds to identifying core elements of homologous molecules. HMMs can also provide additional information such as the probability of initiating an insertion at any position in the model, and the probability of extending it. The structure of an HMM is similar to that of a profile, with position-specific insert and delete probabilities. In constructing an HMM or profile for the subfamilies, information can be shared between subfamilies at positions where there is evidence of common structural constraints.

The HMM for canonical base sequence determinations typically contains 1024 states, one for each possible 5-mer. HMM for analysis of abasic sites will include additional states for 5-mers containing abasic sites. The software as described here takes advantage of characteristic current increases when the bases of interest are converted to an abasic site. These changes in ionic current permit determination of the location of modified bases of interest. The UCSC Nanopore group has previously developed software to detect cytosine modifications within otherwise canonical DNA sequences (Schreiber et al, Proc Natl Acad Sci USA. 2013, 110:18910-5; Wescoe et al, J Am Chem Soc. 2014, 136:16582-7). These papers, combined with the present description enable the creation of a custom bioinformatics package to develop the aforementioned software. The combination of the described method, software, and nanopore-based sequencing can be used to perform de novo calling and identification of bases (canonical or modified).

Example 2: Proof that Significant Differences are Obtained from Abasic Sites in Sequence Referring now to FIG. 4A-4D, the distributions of mean currents for segments from base calling events in the MINION™ sequencer for the four PCR reactions are shown.

FIG. 4A shows the results of a control Lambda fragment; FIG. 4B shows current distributions for control Lambda fragment glycosylase treated; FIG. 4C shows current distributions for control Lambda fragment with dUTP; and FIG. 4D shows current distributions for control Lambda fragment with dUTP and glycosylase treatment Current levels as shown in FIG. 4A-4D were used to determine DNA base identity in MINION™ nanopore sequencing. Abasic positions are associated with a high current relative to positions within a DNA strand that contain a base. Currents in the range of approximately 100 pA are found to a significant degree only in the graph of FIG. 4D. Only the reaction in FIG. 4D is expected to contain abasic sites. Note the peak at high current levels revealed as a spike on the shoulder of the current level distribution circled in 4D and its absence in FIGS. 4A, 4B and 4C.

Referring now to FIG. 5A, 5B, there is illustrated an example of data for a control polynucleotide and an abasic polynucleotide. FIG. 5A is a nanopore sequencing result (raw data) from a non-treated DNA expected to have no abasic sites. FIG. 5B shows similar DNA containing U and then treated with a Uracil DNA glycosylase to generate abasic sites. Shown are data from DNA strands processed in MINION™ nanopore sequencing runs. Depicted in panels 5A and 5B are MINION™ raw data current traces. The panel 5A is from a Control lambda DNA strand containing the 4 canonical DNA bases (ACGT) and no abasic sites. The panel 5B is from a lambda DNA strand that also has Uracil incorporated into it, and then was subsequently treated with Uracil DNA glycosylase to generate abasic sites at positions of T within the sequence. In panel A, current traces corresponding to the canonical sequence of the lambda strand do not exceed 90 pA current (straight line at about 90 pA). The high current spikes at time equals 3820 seconds and approximately 3822 seconds are sequencer imposed currents. Similarly the high current seen at time equals 3852 seconds is from the adaptor used in library preparation of DNA for sequencing. In panel 5B, the current trace for a lambda DNA strand containing abasic sites, current is seen to exceed 90 pA at positions of T within the sequence marking abasic sites.

Example 3: Creation of Abasic Sites in Place of 5-Methylcytosine

FIG. 6 shows one of several best ways of creating abasic sites, in particular for epigenetic sequencing using the MINION™ nanopore device. Shown there are two approaches to sequencing DNA to determine positions of the epigenetic marker 5-methylcytosine. In approach I, a 5-methylcytosine specific DNA glycosylase is used to generate abasic sites at base positions originally containing 5-methylcytosine. The position of the abasic site is determined by the nanopore sequencer and confirmation of the correct position is made by sequence on the opposite strand, i.e. of a G base which paired with the 5-methylcytosine before glycosylase treatment. In approach 2, the 5-methylcytosine is first enzymatically deaminated to thymine by 5-methylcytosine deaminase. Subsequent treatment with G/T(U)-mismatch DNA glycosylase removes the thymine, generating an abasic site for detection by the MINION™ nanopore sequencer. The example sequences shown have the sequences ACCCG-TAACabasicGGATTCGCGTAAA (approach I, strand with abasic site; SEQ ID NO: 5), ACCCGTAACTGGAT-TCGCGTAAA (approach II, strand with T/G mismatch; SEQ ID NO: 6), and TTTACGCGAATCCGGTTACGGGT (complementary strand in both approaches; SEQ ID NO: 7).

Example 4: Creating Abasic Sites to Improve Analysis of Regions of Sequencing Difficulty Various sequencing processes encounter difficulty with regions of repetitive bases. It is difficult to determine the number of bases in homo-polymeric runs or short repeats. FIG. 7A shows one of several best ways of improving sequence accuracy, specifically, in this example, for determining homo-polymeric runs of Ts. In this example, one uses initial replication of the DNA to be sequenced using a high fidelity polymerase and a mixture of the 4 canonical bases (ACGT) and dUTP. DNA is then treated with a Uracil DNA glycosylase and a sequencing library prepared from this material. The sequences for individual DNA strands are then aligned with each other noting positions of abasic sites. Contiguous blocks of abasic positions are identified and used to determine the length of homo-polymeric runs of Ts and As. In the figure, only bases in the homopolymeric stretch are indicated with explicit bases; the other base pairs are represented with vertical lines connecting the two strands. The steps may also be summarized as follows:

| Step 1 | Use DNA polymerase to replicate the DNA sequence using dATP, dCTP, dGTP, dTTP and dUTP |
| --- | --- |
| Step 2 | Use Uracil DNA glycosylase to create abasic sites at sites of incorporated Uracil |
| Step 3 | Determine base positions of abasic sites using the MinION |
| Step 4 | Align sequences and identify contiguous blocks of abasic sites in pile ups |
| Step 5 | Homopolymeric runs of Ts are identified based on abasic positions in the consensus sequence |

A similar approach is detailed for homo-polymer runs of C's and G's in FIG. 7B. The steps may be summarized as:

| Step 1 | Copy DNA to be analyzed with 1-X cycles of PCR |
| --- | --- |
| Step 2 | Treat w/ DNA Glycosylase engineered to remove cytosines and create abasic positions at cytosine |
| Step 3 | Determine base positions of abasic sites using a nanopore sequencer. Determine Kmers containing abasic sites w/ nanopore sequencer |
| Step 4 | Align sequences |
| Step 5 | Integrate read information to determine length of homopolymeric run of Cs |

These methods can also be used to improve sequencing accuracy outside of homopolymeric tracts.

As described below also in connection with FIG. 10, FIG. 7C, 7D shows a similar approach for detecting certain bases that can be replaced with bases that are glycosylase substrates. A complementary strand is made, and a hairpin is used to connect these two strands. The ligated strand is then copied with substituted bases, e.g. U replacing T. The U's are removed by uracil-DNA glycosylase treatment. The sequencing thus produces a duplex molecule with one strand containing abasic sites and a complementary strand that can be used to confirm sequence data. FIG. 7C shows the step of ligating a DNA hairpin to one end of DNA and a sequencing adapter to the other end of DNA, followed by a step of copying both strands of the DNA with a DNA Polymerase using one or more modified base(s) (X) as a substitute for one or more of the 4 canonical bases (ACGT). In this example the modified base is uracil which replaces T and basepairs with A. FIG. 7D shows the step of treating DNA with Uracil DNA Glycosylase. In FIG. 7C, 7D, only bases in locations of replacement are indicated with explicit bases; the other base pairs are represented with vertical lines connecting the two strands.

In addition, one may use the present methods to detect 5-methylcytosine (5mC) in genomic DNA (gDNA) with a nanopore with other base modification strategies:

Method 1:

5mC can be converted to 5-carboxylcytosine (5caC) via an oxidation reaction using the enzyme Tet1 (commercially available as part of a kit: http (colon slash slash)/www(dot)wisegeneusa.com/#!Tet1/c12zy). Thymine DNA glycosylase (TDG) will then excise the resulting 5caC, thus creating an abasic site that can be detected using a nanopore and mapped using custom-designed software.

Method 2:

Bisulfite treatment of DNA results in conversion of a canonical Cytosine (C) to a Uracil (U) which can then be converted to an abasic residue using Uracil DNA glycosylase. This process does not affect 5mC. However, 5mC can be converted to C by treating DNA with a demethylase enzyme (like this one available as part of a kit: http (colon slash slash) www(dot) epigentek.com/catalog/epiquik-dna-demethylase-activityinhibition-assay-ultra-kit-p-3440.html). To do this one would split the gDNA in two reactions.

For the first reaction, bisulfite treatment of gDNA will convert C's to U's, and then the resulting U's to abasic sites using UDG. This will leave the 5mC's unaffected. The resulting abasic sites can be detected using a nanopore and mapped using custom-designed software. These sites will indicate the presence of C's in gDNA.

For the second reaction, first convert 5mC's in genomic DNA to C's using a demethylase, and then perform bisulfite treatment to convert all C's (original C's as well as the 5mC's that were converted) to U's. These U's will convert to abasic sites using UDG. The abasic sites can be detected using a nanopore and mapped using custom-designed software. These sites will indicate the presence of C's as well as 5mC's in gDNA.

Custom designed software to use information from the two reactions will help discern the presence and location of 5mC's in gDNA.

Example 5: Improving RNA Sequencing by Creating Abasic Sites at Specific Points

FIG. 8 illustrates a method for improving RNA sequencing using abasic sites. Briefly, an RNA molecule can be reverse transcribed to form a cDNA-RNA hybrid. Nucleotide incorporation is performed using dNTP's, but with dUTP substituting for dTTP. The resulting cDNA that contains dUTP can be then treated by Uracil DNA Glycosylase to form abasic sites that can be detected using a nanopore-based sequencer that will provide further data on the RNA sequence, which will be sequenced both directly as RNA and as a complementary treated DNA strand that contains abasic sites at known locations. RNA that may be sequenced includes but is not limited to mRNA (messenger RNA), tRNA (transfer RNA), and rRNA (ribosomal RNA). "X" in this example represents dUTP incorporation in DNA complementary to A in the RNA but may also be other substitutions which can be removed by a specific DNA glycosylase. The example sequences shown have the sequences UCCCGUGGCCGUAGGCGCGUCGG (RNA strand to be sequenced; SEQ ID NO: 8), CCGACGCGC-CXACGGCCACGGGA (cDNA strand with non-standard base "X", uracil in the present example; SEQ ID NO: 9), and CCGACGCGCCabasicACGGCCACGGGA (cDNA strand with abasic site; SEQ ID NO: 10).

Example 6: Epigenetic Analysis of Base Modifications

There is presently a need for determining modifications that are not attributable to changes in the primary DNA sequence. Epigenetic modifications play a crucial role in gene expression, and thereby underpin the development, regulation, and maintenance of the normal cell. A commonly studied epigenetic modification is the methylation of cytosine (C) nucleotides in the context of a CpG dinucleotide. Historically, restriction enzymes have been used as one method to detect DNA methylation. The present methods can yield simultaneous sequencing and base modification determinations in a defined work flow using base enzymatic modification and nanopore-based sequencing.

Shown in FIG. 9 are structures of cytosine and modified cytosines. A sample under study can be treated with a series of enzymatic modifications to produce new bases in the sequence; these new bases are substrates for known glycosylases which then produce abasic sites that are analyzed as described above. Shown below is a work flow for detecting and distinguishing cytosine, 5-methylcytosine (5mC), 5-hydroxymethylcytosine (5hmC), 5-formyl (5fC) and 5-carboxycytosine (5caC) in a single polynucleotide.

To detect a variety of modified cytosine bases, one treats aliquots of DNA to be sequenced as follows:

5mC→5-methylcytosine DNA glycosylase→abasic site; or
5mC→convert to T/U mismatch using 5-methylcytosine deaminase→G/T(U) mismatch DNA glycosylase→abasic site
5hmC+KRuO4→5fC→thymine DNA glycosylase→abasic site
5fC→thymine DNA glycosylase→abasic site
5caC→thymine DNA glycosylase→abasic site.

The use of $KRuO_4$ (potassium perruthenate) and the use of this chemical for conversion of 5-hydroxymethylcytosine to 5-formylcytosine are further described in "Quantitative Sequencing of 5-Methylcytosine and 5-Hydroxymethylcytosine at Single-Base Resolution," Booth et al. Science 336 (6083) 934-937 (May 2012) and "Oxidative bisulfite sequencing of 5-methylcytosine and 5-hydroxymethylcytosine," Booth et al., Nat. Protocol. 8(10): 1841-1851 (October 2013).

As above, the abasic sites are in predetermined points in the polynucleotide sequence, and can be readily determined by the sequencing signal from an abasic site.

Example 7: 5-Methylcytosine Detection with Sequencing of Template and Complement Strands Using a DNA Hairpin and Strand Replication with a DNA Polymerase As described above, the present methods may be used to detect epigenetic modifications such as 5-methylcytosine. FIG. 9 (discussed above) shows different modified cytosines that can be treated and identified using the present methods. In this example, DNA to be sequenced is copied by a DNA polymerase to provide a canonical copy and a copy with abasic positions at sites of 5mC all in one contiguous DNA strand (FIG. 10) for nanopore sequencing. The first step involves ligation of a primer/DNA barcode to one end of the DNA molecule and a low melting DNA hairpin to the other end. The primer/DNA barcode provides a primer sequence for copying the DNA strands and the hairpin provides a mechanism for keeping the original template and complement strands attached to each other during enzymatic copying. The DNA is copied using a single round of PCR to generate strand 1 paired with strand 2 (shown in FIG. 10). Strand 1 (top strand in FIG. 10) is the original template and complementary strands to be sequenced, connected by the linearized hairpin sequence. The hairpin is illustrated as appearing between the template and complementary strands. Each end of the construct consists of a primer/DNA barcode (sequencing adapter sequence). Strand 2 (shown beneath and complementary to strand 1) is a copy of the original duplex molecule and does not contain modified bases, due to the bases used for the copying step. The complex is treated with 5-methylcytosine glycosylase or 5-methylcytosine deaminase and G/t(U)-mismatch DNA glycosylase to create abasic sites in only the original strands at positions of 5-methylcytosine. This results in abasic sites at 5-methylcytosine positions in strand 1 and a copy strand containing only canonical bases in strand 2. Two abasic sites are shown in this example. Only bases in locations where abasic sites are generated are illustrated here; other base pairs are represented with vertical lines connecting the two strands. The samples may be prepared using standard nanopore sequencer commercial library kits that use a hairpin to connect Strands 1 and 2 together for contiguous sequencing of both DNA strands. A nanopore sequencer and sequencing software described above will then determine the positions of the abasic sites in the original DNA strand, and confirm base identity by comparison of the base sequence of the copied strand with the original template and complement strands originally containing the modified bases which have now been converted to abasic positions.

Example 8: Use of DNA Glycosylases and Corresponding Modified Bases Detected Table 1, extracted from Krokan, Standal, and Slupphaug (1997), illustrates a variety of glycosylases that can be used to create abasic sites at predetermined sites in a polynucleotide sequence and thus identify a wide variety of modified bases in a polynucleotide. The column labeled "beta lyase activity" refers to the activity of the enzyme in column 1 in cleaving the polynucleotide. This activity may be removed by engineering the enzyme to remove this activity, while retaining the cleavage activity shown in FIG. 1.

TABLE 1

| Enzyme | Source/Gene | Reported DNA Modified Base Substrates | Beta-Lyase Activity |
|---|---|---|---|
| Uracil-DNA Glycosylase | Viral | Uracil | No |
| | Bacterial/(UNG) | 5-Fluorouracil, Isodiauric Acid, 5-Hydroxyuracil | No |
| | Yeast (S. cerevisiae) (UNG1) | Uracil | No |
| | Plants | Uracil | No |
| | Human(UNG) | 5-Fluorouracil, , Alloxan, 5-Hydroxyuracil | No |
| G/T(U) mismatch-DNA Glycosylase | M. thermoautotropicum | G/G, A/G, T/C, U/C | No |
| | Insects | Uracil mismatch | No |
| | Human | T and U mismatch | No |
| Alkylbase-DNA Glycosylases | E. coli (tag) | 3-methyl guanine | No |
| | E. coli (alkA) | $O^2$-Alkylcytosine, 5-formyluracil, 5-hydroxymethyluracil, hypoxanthine, $N^6$-ethenoadeinine, $N^4$-ethenocytosine | No |
| | S. cerevisiae (MAG) | 7-chloroethyl-guanine, hypoxanthine, $N^6$-ethenoadeinine, | No |
| | S. pombe (mag1) | 3-Methyladenine | Unk. |
| | A. Thaliana (MPG) | 3-Methyladenine | Unk. |
| | Rodent/Human (MPG) | 7-chloroethyl-guanine, 8-oxoguanine hypoxanthine, $N^6$-ethenoadeinine, | No |
| 5-Methylcytosine-DNA Glycosylase | Chick Embryo | T in G/T mismatch 5-methylcytosine | No No |
| Thymine DNA Glycosylase | Human (TdG) | 5-formylmethylcytosine (5fC) | No |
| | Human (TdG) | 5-carboxylcytosine (5caC) | |
| Adenine-specific mismatch DNA Glycosylases | E. coli (mutY) | A in G/A and C/A | Yes/No |
| | Bovine, Human (MYH) | A in G/A and CA also 8-oxoguanine | Yes |
| DNA Glycosylases removing oxidized pyrimidines (EndoIII-like) | E. coli EndoIII (nth) | 5-hydroxycytosine, 5,6-Dihydrothymine, 5-Hydroxy-5,6-dihydrothymine, Thymine glycol, Uracil glycol, Alloxan, 5,6-Dihydroxyuracil, 5-Hydroxy-5,6-dihydroxyuracil, 5-Hydroxyuracil, 5-Hydroxyhydantoin | Yes |
| | S. cerevisiae (NTG1) | 2,5-Amino-5-formamidopyrimindine, 4,6-Diamino-5-formamidopyrimidine, 2,6-Diamino-4-hydroxy-5-foramimidopyrimidine, Thymine glycol | Yes |
| | S. pombe (nth) | Thymine glycol, 5-Hydroxy-uracil | Yes |
| | Bovine/human EndoIII | Thymine glycol | Yes |
| EndoVIII | E. coli | 5,6-Dihydrothymine, Thymine glycol | Yes |
| EndoIX | E. coli | Urea | Unk. |
| Hydroxymethyl-DNA glycosylase | Mouse | Uracil | No |
| | Bovine | 5-hydroxymethyluracil | Unk. |
| Formyluracil-DNA glycosylase | Human | 5-formyluracil | Unk. |
| DNA glycosylases removing | E. coli (fpg) | 8-oxoguanine, 2,5-Amino-5-formamidopyrimidine, | Yes |

TABLE 1-continued

| Enzyme | Source/Gene | Reported DNA Modified Base Substrates | Beta-Lyase Activity |
|---|---|---|---|
| oxidized purines | | 4,6-Diamino-5-formamidopyrimidine, 2,6-Diamino-4-hydroxy-5-foramimidopyrimidine | |
| | S. cerevisiae (OGG1) | 8-oxoguanine (opposite T) | Yes |
| | S. cerevisiae (OGG2) | 8-oxoguanine (opposite A) | Yes |
| | D. melanogaster S3 | 8-oxoguanine | Yes |
| Pyrimidine-dimer-DNA glycosylases | T4 | 4,6-Diamino-5-formamidopyrimidine | Yes |
| | M. luteus | Cyclobutane-pyrimidine dimer | Yes |
| | | N. mucosa | Yes |

A more recent list of glycosylase enzymes is included in Table 2.

TABLE 2

DNA Glycosylases Extracted from - Recent Advances in the structural mechanisms of DNA glycosylases. Brooks et al. 2013.

| Gene Symbol | Source |
|---|---|
| OGG1 | Eukaryotes |
| | Archaea |
| | Prokaryotes |
| OGG2 | Eukaryotes |
| AGOC | Archaea |
| MutM/Fpg | Prokaryotes |
| NTH1 | Eukaryotes |
| EndoIII | Archaea |
| Nth/EndoIII | Prokaryotes |
| NEIL1 | Eukaryotes |
| Nei/EndoVIII | Prokaryotes |
| NEIL2 | Eukaryotes |
| NEIL3 | Eukaryotes |
| AAG | Eukaryotes |
| MAG1 | Eukaryotes |
| AfA1kA | Archaea |
| MpgII | Archaea |
| AlkA | Prokaryotes |
| MagIII | Prokaryotes |
| TAG | Prokaryotes |
| AlkC | Prokaryotes |
| AlkD | Prokaryotes |
| MUTYH | Eukaryotes |
| MutY | Archaea |
| MutY | Prokaryotes |
| UDG | Eukaryotes |
| Ung | Archaea |
| UDG-1 | Prokaryotes |
| SMUG | Eukaryotes |
| UDG-3 | Prokaryotes |
| TDG | Eukaryotes |
| MUG | Archaea |
| UDG-2 | Prokaryotes |
| UDG | Archaea (Thermus thermophiles) |
| UDG-4 | Prokaryotes |
| MBD4 | Eukaryotes |
| MIG | Archaea |
| DME | Eukaryotes |
| ROS1 | Eukaryotes |
| DML2 | Eukaryotes |
| DML3 | Eukaryotes |

Example 9: Engineering of DNA Glycosylases Including Removal of their Beta-Lyase Activity and Changing Specificity It is preferred that the glycosylases used herein do not contain beta lyase activity, i.e. do not cleave the strand when excising the base to be removed. The DNA glycosylases listed above can be modified by routine experimentation to lack the beta lyase activity. This is described, e.g. in:

Recent advances in the structural mechanisms of DNA glycosylases. Brooks, Sonja C.; Adhikary, Suraj; Rubinson, Emily H.; and Eichman, Brandt F. Biochimica et Biophysica Acta-Proteins and Proteomics Volume: 1834 Issue: 1 Pages: 247-271 Published: January 2013; Base Excision Repair. Krokan, Hans E.; Bjoras, Magnar. Cold Spring Harbor Perspectives in Biology 5(4) Number: a012583, April 2013; "DNA glycosylases in the base excision repair of DNA," Krokan, H E; Standal, R; Slupphaug, G. Biochemical Journal Volume: 325 Pages: 1-16 Part: 1 Published: Jul. 1, 1997.

Briefly, the glycosylase of interest will be part of one of two classes of enzymes, having known mechanisms of activity. The first class is mono-functional and cleaves the base from the sugar phosphate backbone by cleavage of the N-glycosidic bond to yield a free base and an abasic site in the DNA or RNA strand. The second group of bifunctional glycosylases has both base cleavage activity and beta-lyase activity (cleavage of the sugar phosphate backbone). The above papers describe glycosylases in general and include information needed for engineering the second group of enzymes to eliminate beta lyase activity and in turn make these enzymes more useful in nanopore sequencing of nucleic acids with modified bases. The bi-functional enzymes are believed to involve an intermediate in which the sugar phosphate backbone is covalently linked to the glycosylase, whereas the mono-functional glycosylase class does not proceed using this mechanism. Additionally, the mechanism for generation of the nucleophilic intermediate responsible for base cleavage differs between these two classes of glycosylases. The amino acid residues involved in generation of a nucleophile for base cleavage (as well as covalent attachment of enzyme to sugar phosphate backbone) are different between the bi-functional glycosylases and the mono-functional glycosylases. Our approach is to engineer the bi-functional glycosylases using site directed mutagenesis, to change those amino acid residues involved in either nucleophile generation for base cleavage or points of covalent attachment of the bi-functional glycosylase to the sugar phosphate backbone as an intermediate in the reaction mechanism or both.

In addition, a known enzyme can be altered to change its substrate. In site directed mutagenesis of human uracil DNA glycosylase, conversion of Tyr147 to Ala147 resulted in the human UDG cleaving both uracil and thymine. This could be a method for improving sequence accuracy by direct treatment of the DNA with this mutant glycosylase followed by sequencing (which would allow resolution of homopolymer tracts of T's and A's). Similarly, changing Asn204 to Asp204 results in the glycosylase cleaving both uracil and cytosine. This would also potentially improve sequencing accuracy. This is described in "Excision of cytosine and thymine from DNA by mutants of human uracil-DNA glycosylase," Kavli, B; Slupphaug, G; Mol, C D; et al. EMBO JOURNAL Volume: 15 Issue: 13 Pages: 3442-3447 Published: Jul. 1, 1996.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

What is claimed is:

1. A method for detecting epigenetically modified cytosines in genomic DNA, wherein the epigenetically modified cytosines comprise 5-methylcytosine (5mC), 5-hydroxymethylcytosine (5hmC), 5-formylcytosine (5fC) and 5-carboxylcytosine (5caC), the method comprising:

(a) treating genomic DNA comprising or suspected of comprising the epigenetically modified cytosines with a 5-methylcytosine deaminase that acts on 5mC to create a T/U mismatch;

(b) treating the genomic DNA treated in (a) with a G/T(U) mismatch DNA glycosylase that acts on the T/U mismatch to create an abasic site in the genomic DNA; and (c) conducting single molecule nanopore sequencing on the genomic DNA prepared in step (b), including determining a sequence that comprises the abasic site based on the ionic current of the abasic site, thereby detecting epigenetically modified cytosines in genomic DNA.

2. The method of claim 1, wherein the steps (a)-(c) are conducted on a first aliquot of the genomic DNA and the method further comprises:

(d) treating a second aliquot of the genomic DNA comprising or suspected of comprising the epigenetically modified cytosines with:

(i) a 5-methylcytosine DNA glycosylase that acts on 5mC to create an abasic site in the genomic DNA;

(ii) KRuO4 that acts on 5hmC to create 5fC, and further treating the genomic DNA treated in (d)(ii) with a thymine DNA glycosylase that acts on 5fC to create an abasic site in the genomic DNA, or (iii) a thymine DNA glycosylase that acts on 5fC and 5caC to create an abasic site in the genomic DNA; and (e) conducting single molecule nanopore sequencing on the genomic DNA prepared in step (d), including determining a sequence that comprises the abasic site based on the ionic current of the abasic site, thereby detecting epigenetically modified cytosines in the genomic DNA.

3. The method of claim 2, wherein the method comprises step (d)(i).

4. The method of claim 3, wherein the steps (a)-(c) are performed prior to steps (d)-(e) or simultaneously.

5. The method of claim 3, wherein the steps (d)-(e) are performed prior to steps (a)-(c) or simultaneously.

6. The method of claim 2, wherein the method comprises step (d)(ii).

7. The method of claim 6, wherein the steps (a)-(c) are performed prior to steps (d)-(e) or simultaneously.

8. The method of claim 6, wherein the steps (d)-(e) are performed prior to steps (a)-(c) or simultaneously.

9. The method of claim 2, wherein the method comprises step (d)(iii).

10. The method of claim 9, wherein the steps (a)-(c) are performed prior to steps (d)-(e) or simultaneously.

11. The method of claim 9, wherein the steps (d)-(e) are performed prior to steps (a)-(c) or simultaneously.

12. The method of claim 2, wherein the method comprises two or more of steps (d)(i)-(d)(iii), wherein the two or more steps are performed on separate aliquots of the genomic DNA.

* * * * *